United States Patent
McClellan et al.

(10) Patent No.: US 9,113,975 B2
(45) Date of Patent: Aug. 25, 2015

(54) STERNUM BAND TENSIONER DEVICE, SYSTEM AND METHOD

(75) Inventors: William Thomas McClellan, Morgantown, WV (US); John F. Krumme, Woodside, CA (US); Scott H. Heneveld, Whitmore, CA (US)

(73) Assignee: Figure 8 Surgical, Inc, Palo Alto, CA (US)

( * ) Notice: Subject to any disclaimer, the term of this patent is extended or adjusted under 35 U.S.C. 154(b) by 442 days.

(21) Appl. No.: 13/526,420

(22) Filed: Jun. 18, 2012

(65) Prior Publication Data

US 2012/0323241 A1 Dec. 20, 2012

Related U.S. Application Data

(60) Provisional application No. 61/498,508, filed on Jun. 17, 2011.

(51) Int. Cl.
*A61B 17/82* (2006.01)
*A61B 17/84* (2006.01)
*A61B 17/88* (2006.01)

(52) U.S. Cl.
CPC ......... *A61B 17/8869* (2013.01); *A61B 17/8861* (2013.01); *A61B 17/823* (2013.01); *A61B 17/842* (2013.01)

(58) Field of Classification Search
CPC .. A61B 17/7053; A61B 17/82; A61B 17/823; A61B 17/842; A61B 17/8861; A61B 17/8869
USPC ............ 606/263, 74, 99, 103, 105; 140/93.2, 140/123.5, 123.6; 254/243, 245, 246, 250, 254/251, 253, 254, 256
See application file for complete search history.

(56) References Cited

U.S. PATENT DOCUMENTS

| | | | |
|---|---|---|---|
| 1,365,493 A | 1/1921 | Hedger |
| 1,463,213 A | 7/1923 | Hueseman |
| 1,987,527 A | 1/1935 | Frank |
| 2,089,474 A | 8/1937 | Glick |
| 2,128,041 A | 8/1938 | Epstein |
| 2,746,324 A | 5/1956 | Beardsley |
| 2,981,994 A | 5/1961 | White |
| 3,129,919 A | 4/1964 | Evans |
| 3,258,040 A | 6/1966 | Evans |
| 3,528,142 A | 9/1970 | Valdemar |

(Continued)

FOREIGN PATENT DOCUMENTS

| | | |
|---|---|---|
| WO | WO 96/04871 A1 | 2/1996 |
| WO | WO 96/41581 A1 | 12/1996 |

OTHER PUBLICATIONS

Synthes, Inc.; Technique Guide—Sternal ZipFix System; 26 pgs.; Jun. 2011.

*Primary Examiner* — Michael T Schaper
(74) *Attorney, Agent, or Firm* — Andrew D. Wright; Roberts Mlotkowski Safran & Cole, P.C.

(57) ABSTRACT

The invention provides systems and methods for sternum repair. A sternum repair device may include a central body, which may include a plurality of bands and buckles, such that a band extends from the central body and is received by a buckle component. The band may wrap around the sternum and the device may be tightened to keep the separate sternum pieces together. Various band tensioning devices, systems and methods are disclosed.

20 Claims, 37 Drawing Sheets

(56) References Cited

U.S. PATENT DOCUMENTS

| | | | | |
|---|---|---|---|---|
| 3,570,497 A | | 3/1971 | Lemole | |
| 3,584,525 A | | 6/1971 | Caveney et al. | |
| 3,589,406 A | * | 6/1971 | Moberg | 140/93 A |
| 3,641,629 A | | 2/1972 | Beardsley | |
| 3,661,187 A | | 5/1972 | Caveney | |
| 3,712,346 A | * | 1/1973 | Noorily | 140/123.6 |
| 3,782,426 A | * | 1/1974 | Morgan et al. | 140/123.6 |
| 3,810,499 A | * | 5/1974 | Benfer | 140/123.6 |
| 3,830,263 A | * | 8/1974 | Benfer | 140/93.2 |
| 3,837,373 A | | 9/1974 | Beardsley | |
| 3,865,156 A | | 2/1975 | Moody et al. | |
| 3,872,547 A | | 3/1975 | Caveney et al. | |
| 3,946,769 A | | 3/1976 | Caveney et al. | |
| 3,976,108 A | | 8/1976 | Caveney et al. | |
| 4,004,618 A | | 1/1977 | Turek | |
| 4,093,005 A | * | 6/1978 | Eberhardt et al. | 140/123.6 |
| 4,410,019 A | * | 10/1983 | Suzuki | 140/123.6 |
| 4,473,925 A | | 10/1984 | Jansen | |
| 4,498,506 A | | 2/1985 | Moody et al. | |
| 4,510,977 A | | 4/1985 | Crowley | |
| 4,535,764 A | | 8/1985 | Ebert | |
| 4,535,772 A | | 8/1985 | Sheehan | |
| 4,570,340 A | | 2/1986 | Shaw | |
| 4,607,867 A | | 8/1986 | Jansen | |
| 4,646,591 A | | 3/1987 | Jansen | |
| 4,730,615 A | | 3/1988 | Sutherland et al. | |
| 4,793,385 A | * | 12/1988 | Dyer et al. | 140/123.6 |
| 4,813,416 A | | 3/1989 | Pollak et al. | |
| 4,862,928 A | | 9/1989 | Caveney et al. | |
| 4,887,334 A | | 12/1989 | Jansen et al. | |
| 4,896,402 A | | 1/1990 | Jansen et al. | |
| 4,896,668 A | | 1/1990 | Popoff et al. | |
| 4,930,548 A | | 6/1990 | Turek et al. | |
| D309,350 S | | 7/1990 | Sutherland et al. | |
| 4,997,011 A | * | 3/1991 | Dyer et al. | 140/93.2 |
| 5,065,798 A | | 11/1991 | Alletto et al. | |
| 5,072,738 A | | 12/1991 | Wonder et al. | |
| 5,123,456 A | | 6/1992 | Jansen | |
| 5,127,446 A | | 7/1992 | Marelin | |
| 5,129,350 A | | 7/1992 | Marelin | |
| 5,144,989 A | | 9/1992 | Mika et al. | |
| 5,193,250 A | | 3/1993 | Caveney | |
| 5,205,328 A | | 4/1993 | Johnson et al. | |
| 5,286,249 A | | 2/1994 | Thibodaux | |
| 5,303,571 A | | 4/1994 | Quinn et al. | |
| 5,318,566 A | | 6/1994 | Miller | |
| 5,322,091 A | | 6/1994 | Marelin | |
| 5,330,489 A | | 7/1994 | Green et al. | |
| 5,356,412 A | | 10/1994 | Golds et al. | |
| 5,356,417 A | | 10/1994 | Golds | |
| 5,366,461 A | | 11/1994 | Blasnik | |
| 5,368,261 A | | 11/1994 | Caveney et al. | |
| 5,386,856 A | | 2/1995 | Moody et al. | |
| 5,413,585 A | | 5/1995 | Pagedas | |
| 5,423,821 A | | 6/1995 | Pasque | |
| 5,452,523 A | | 9/1995 | Jansen | |
| 5,462,542 A | | 10/1995 | Alesi, Jr. | |
| 5,483,998 A | | 1/1996 | Marelin et al. | |
| 5,488,760 A | | 2/1996 | Jansen | |
| 5,560,045 A | | 10/1996 | Rockefeller | |
| 5,566,726 A | | 10/1996 | Marelin | |
| 5,595,220 A | | 1/1997 | Leban et al. | |
| 5,743,310 A | | 4/1998 | Moran | |
| 5,755,084 A | | 5/1998 | Dekker | |
| 5,766,218 A | | 6/1998 | Arnott | |
| 5,769,133 A | * | 6/1998 | Dyer et al. | 140/123.6 |
| 5,797,916 A | | 8/1998 | McDowell | |
| 5,832,964 A | | 11/1998 | Joshi | |
| 5,850,674 A | | 12/1998 | Jansen | |
| 5,921,290 A | * | 7/1999 | Dyer et al. | 140/123.6 |
| 5,972,006 A | | 10/1999 | Sciaino, Jr. | |
| 6,014,792 A | | 1/2000 | Marelin et al. | |
| 6,030,410 A | | 2/2000 | Zurbrugg | |
| D430,781 S | | 9/2000 | Hillegonds | |
| 6,200,318 B1 | | 3/2001 | Har-Shai et al. | |
| 6,202,706 B1 | | 3/2001 | Leban | |
| 6,206,053 B1 | | 3/2001 | Hillegonds | |
| 6,260,704 B1 | | 7/2001 | Jansen et al. | |
| 6,287,307 B1 | | 9/2001 | Abboudi | |
| 6,354,336 B1 | | 3/2002 | Leban | |
| 6,481,467 B2 | | 11/2002 | Czebatul et al. | |
| 6,516,804 B1 | | 2/2003 | Hoffman | |
| D473,773 S | | 4/2003 | Hillegonds et al. | |
| 6,705,002 B1 | | 3/2004 | Dukes et al. | |
| 6,840,289 B2 | | 1/2005 | Hillegonds | |
| 7,043,315 B2 | | 5/2006 | Litao | |
| 7,089,970 B2 | | 8/2006 | Bernard | |
| 7,124,787 B2 | * | 10/2006 | Lueschen | 140/123.6 |
| 7,168,331 B1 | | 1/2007 | Bernard et al. | |
| 7,216,679 B2 | * | 5/2007 | Magno et al. | 140/123.6 |
| 7,231,944 B2 | * | 6/2007 | Magno et al. | 140/123.6 |
| 7,299,830 B2 | | 11/2007 | Levin et al. | |
| 7,334,610 B2 | | 2/2008 | Levin et al. | |
| 7,361,179 B2 | | 4/2008 | Rousseau et al. | |
| 7,373,695 B2 | | 5/2008 | Caveney et al. | |
| 7,422,037 B2 | * | 9/2008 | Levin et al. | 140/123.6 |
| 7,438,094 B2 | | 10/2008 | Hillegonds et al. | |
| 7,458,398 B2 | | 12/2008 | Hillegonds et al. | |
| 7,484,274 B2 | | 2/2009 | Nelson et al. | |
| 7,591,451 B2 | * | 9/2009 | Dyer et al. | 254/245 |
| 7,600,721 B2 | | 10/2009 | Vermeer et al. | |
| 7,650,680 B2 | | 1/2010 | Stillings et al. | |
| 7,806,895 B2 | | 10/2010 | Weier et al. | |
| 8,029,513 B2 | * | 10/2011 | Konno et al. | 606/103 |
| 2004/0059357 A1 | | 3/2004 | Koseki | |
| 2005/0166990 A1 | | 8/2005 | Stillings et al. | |
| 2005/0178459 A1 | * | 8/2005 | Magno et al. | 140/123.6 |
| 2005/0178461 A1 | * | 8/2005 | Magno et al. | 140/123.6 |
| 2005/0268983 A1 | * | 12/2005 | Levin et al. | 140/123.6 |
| 2006/0037661 A1 | * | 2/2006 | Lueschen | 140/123.6 |
| 2006/0214069 A1 | | 9/2006 | Schiebler | |
| 2006/0254031 A1 | | 11/2006 | DeMik et al. | |
| 2006/0276809 A1 | | 12/2006 | Oliveira | |
| 2007/0021779 A1 | | 1/2007 | Garvin et al. | |
| 2007/0055258 A1 | | 3/2007 | Hansen | |
| 2007/0056145 A1 | | 3/2007 | Stillings et al. | |
| 2007/0290100 A1 | | 12/2007 | Caveney | |
| 2008/0035232 A1 | * | 2/2008 | Levin et al. | 140/123.6 |
| 2009/0078331 A1 | | 3/2009 | DeMik | |
| 2009/0078597 A1 | | 3/2009 | Abbott et al. | |
| 2009/0114308 A1 | | 5/2009 | Marelin et al. | |
| 2009/0121069 A1 | | 5/2009 | Dyer et al. | |
| 2009/0242069 A1 | | 10/2009 | Segroves | |
| 2009/0271956 A1 | | 11/2009 | Nelson et al. | |
| 2010/0139805 A1 | | 6/2010 | Sledzinski | |
| 2011/0022050 A1 | | 1/2011 | McClellan et al. | |
| 2011/0295257 A1 | | 12/2011 | McClellan et al. | |
| 2012/0197256 A1 | * | 8/2012 | Knueppel | 606/74 |
| 2012/0197257 A1 | * | 8/2012 | Knueppel | 606/74 |
| 2012/0265260 A1 | * | 10/2012 | Yamaguchi et al. | 606/86 R |
| 2013/0261625 A1 | * | 10/2013 | Koch et al. | 606/74 |

* cited by examiner

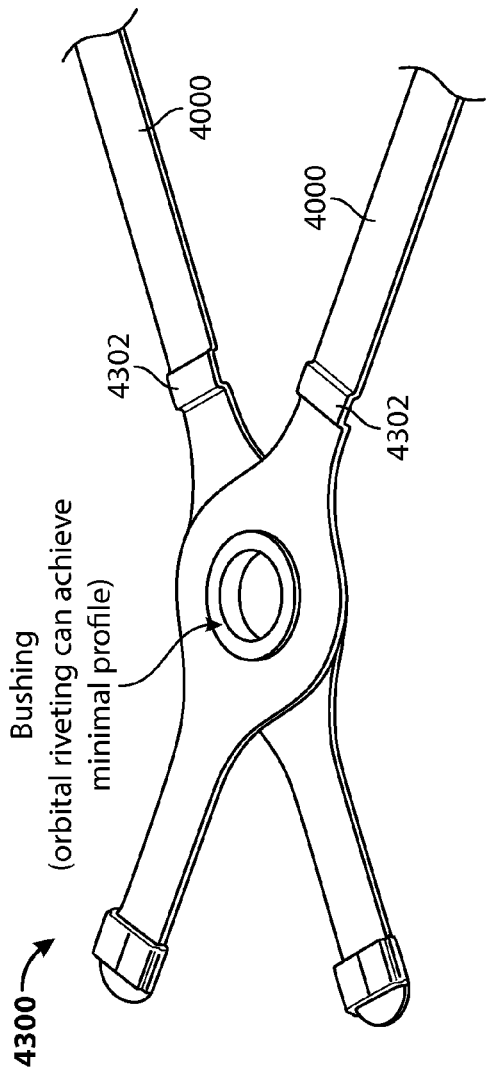
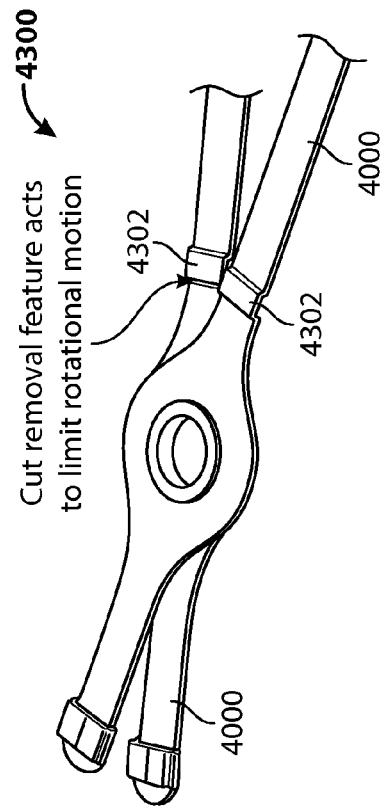
FIG. 8
FIG. 9

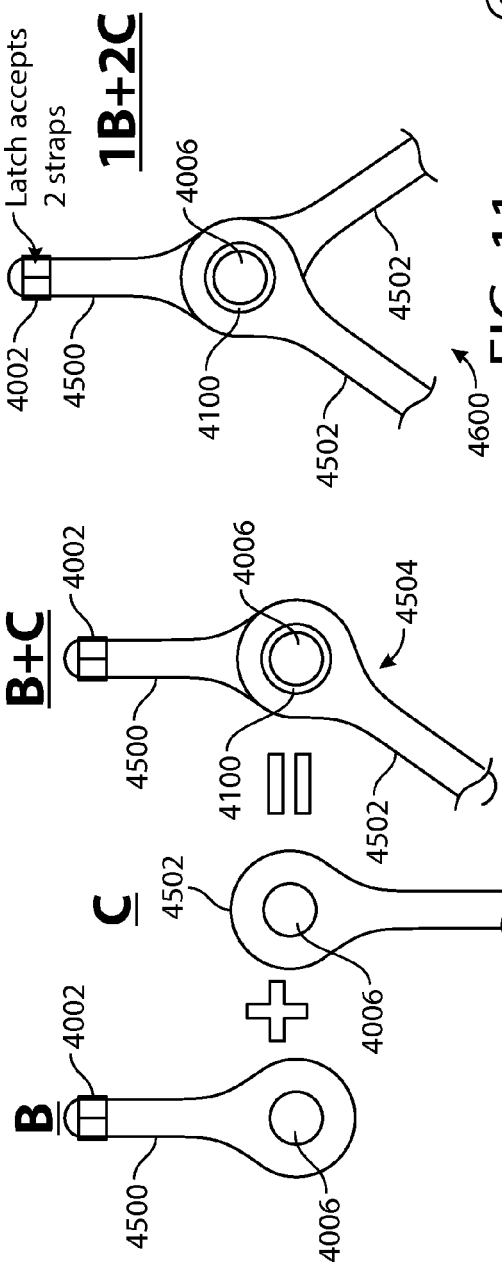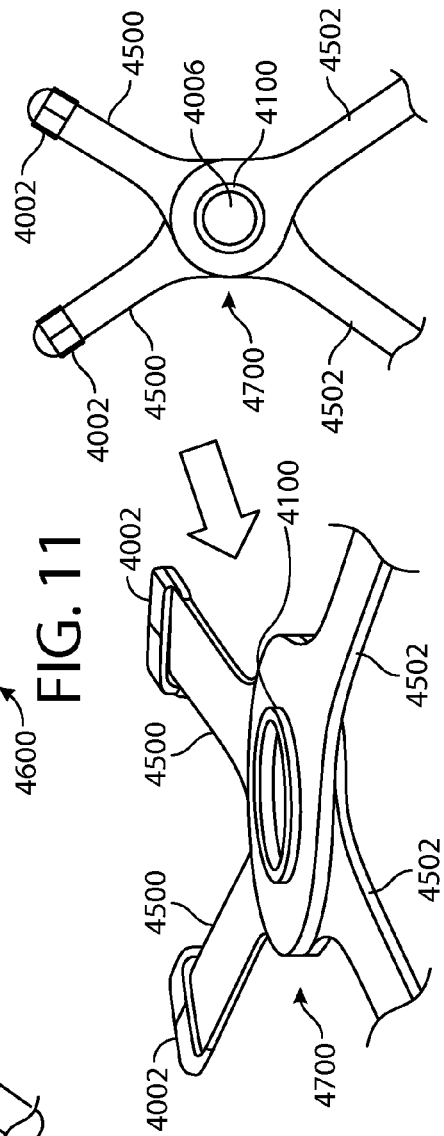

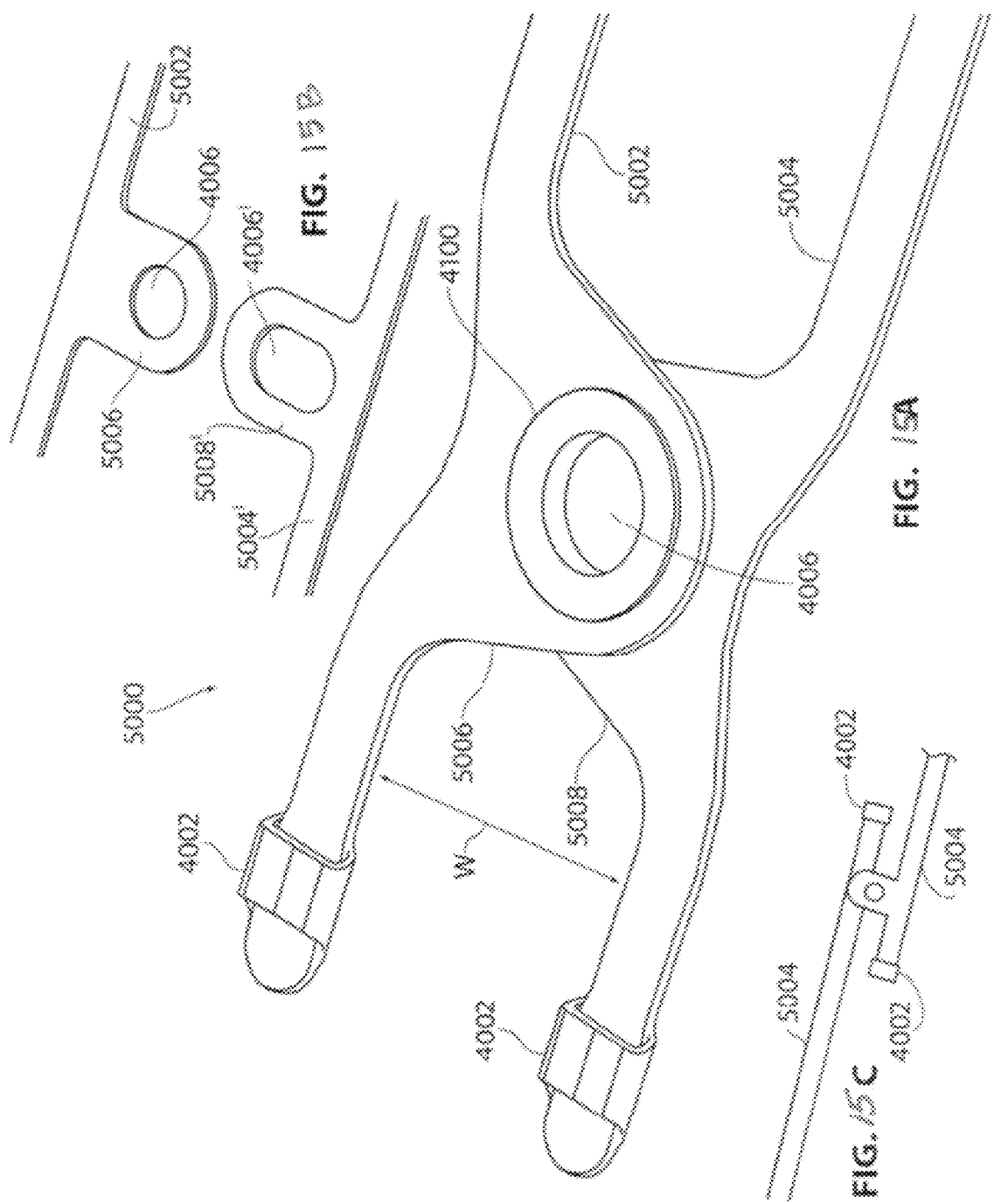

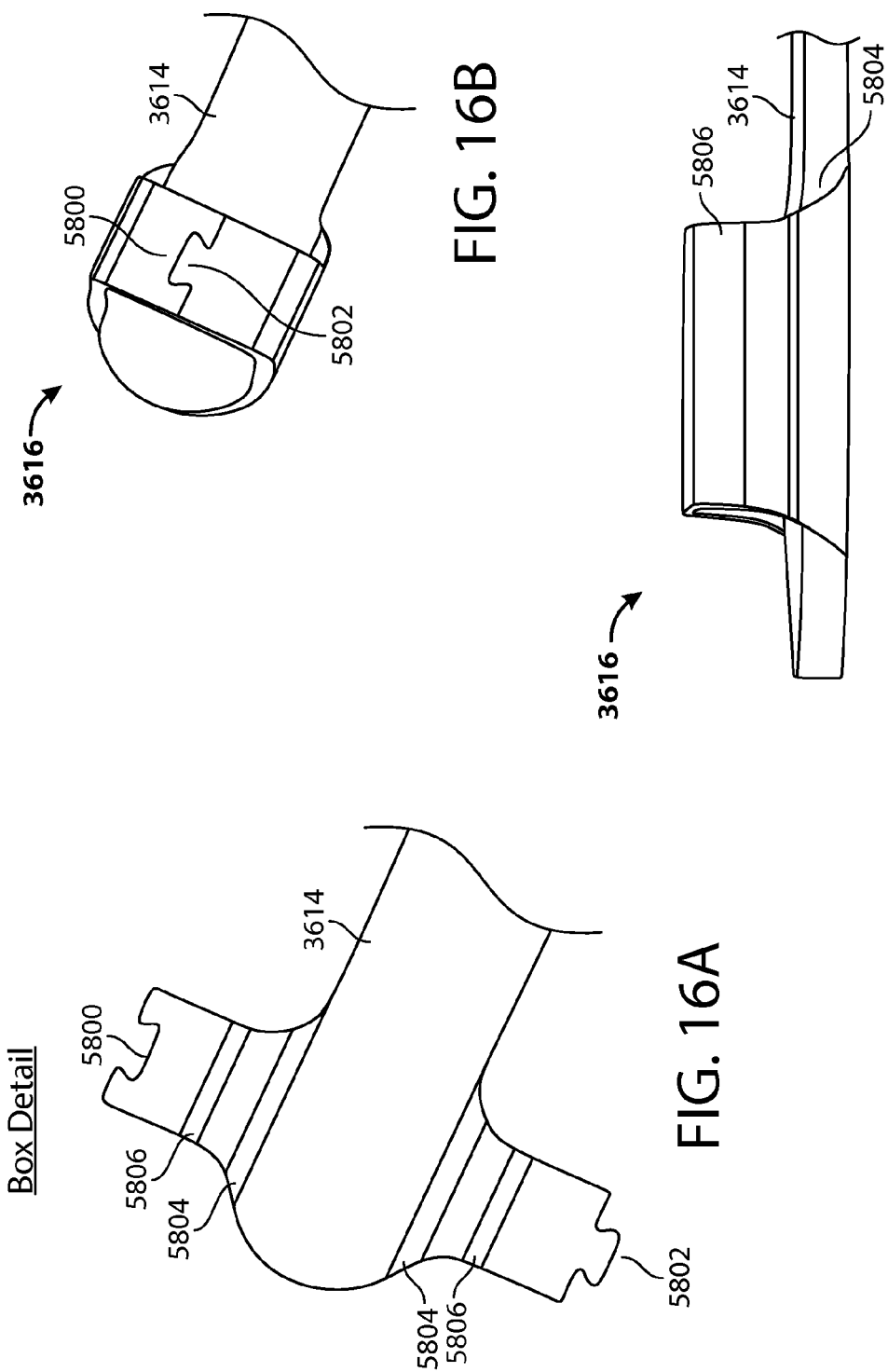

Sternal Closure Device

Tab bent upward

Tab sheared

1b Fold up 180°

Cross Sectional View

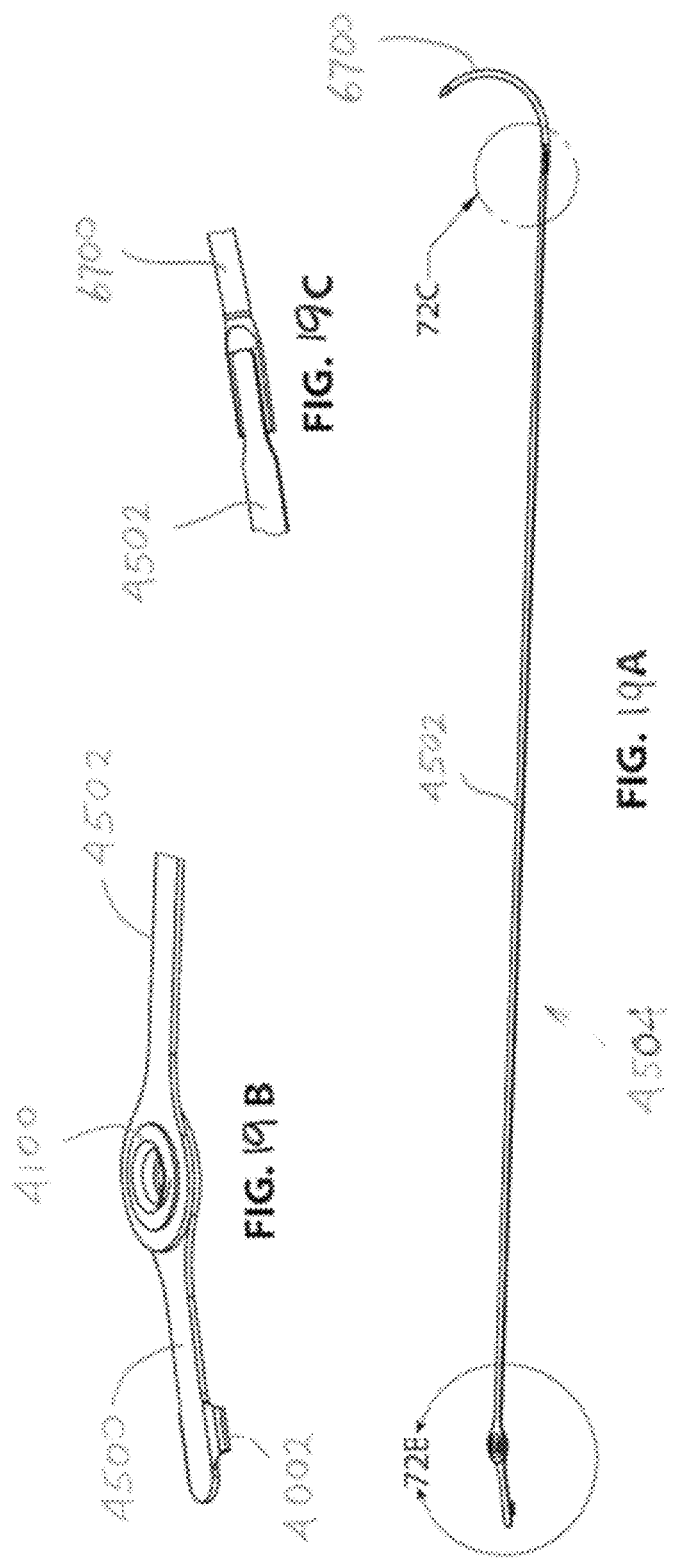

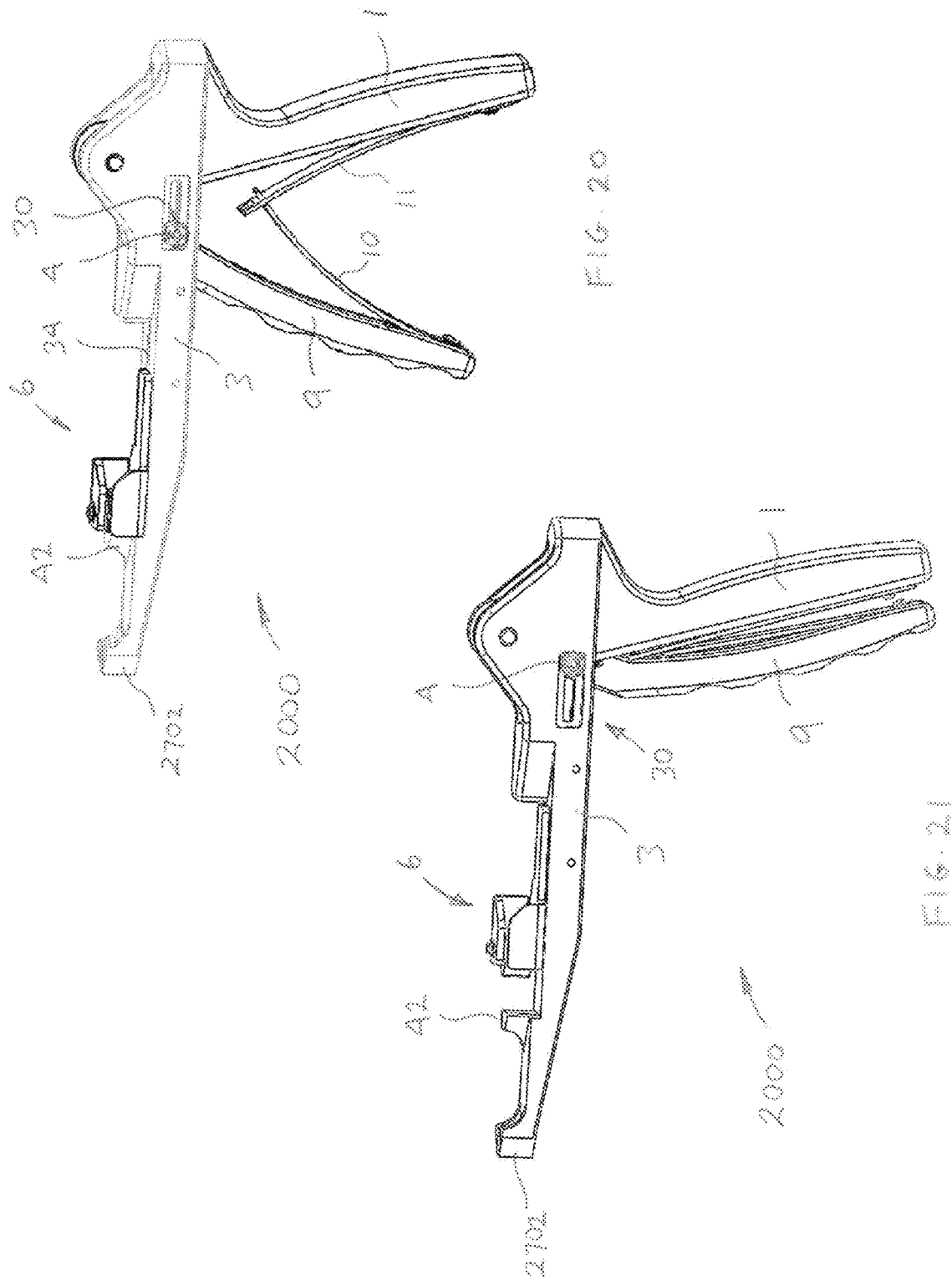

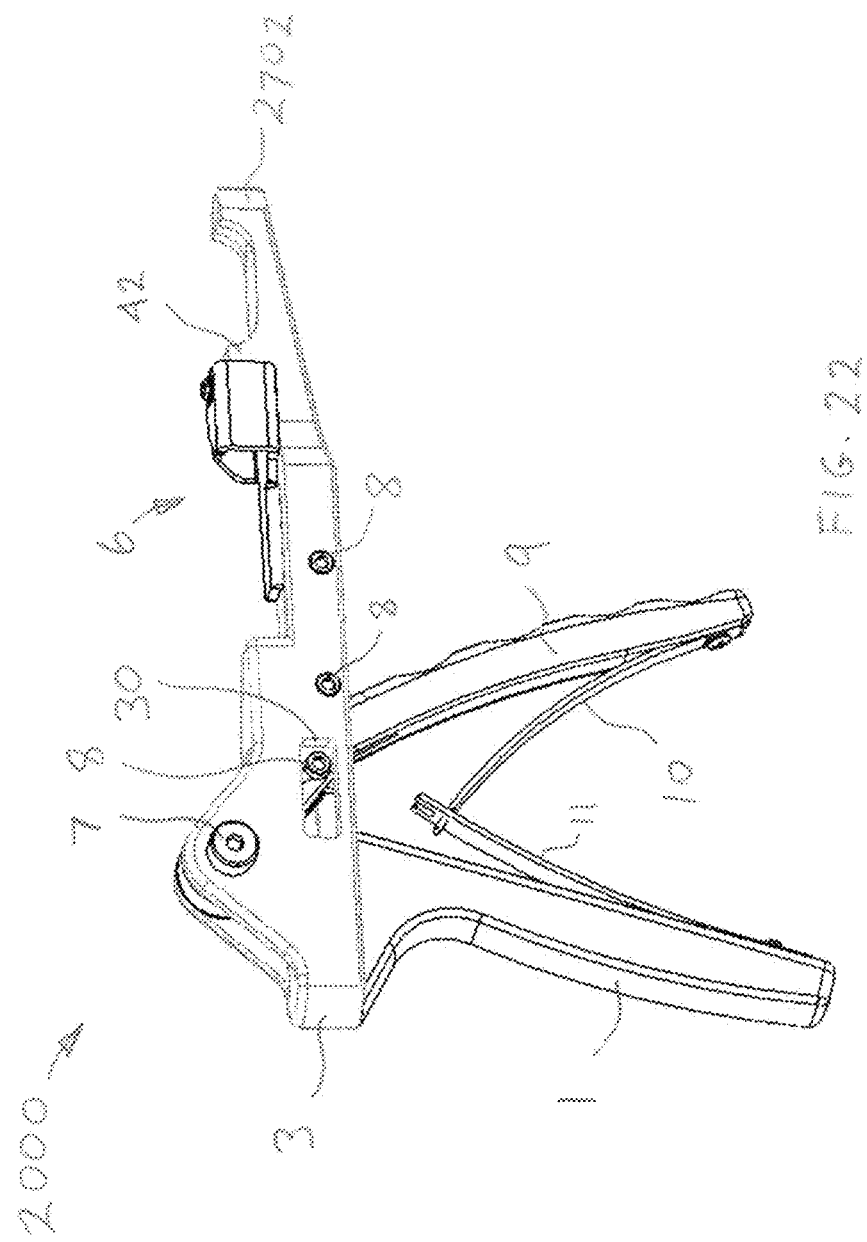

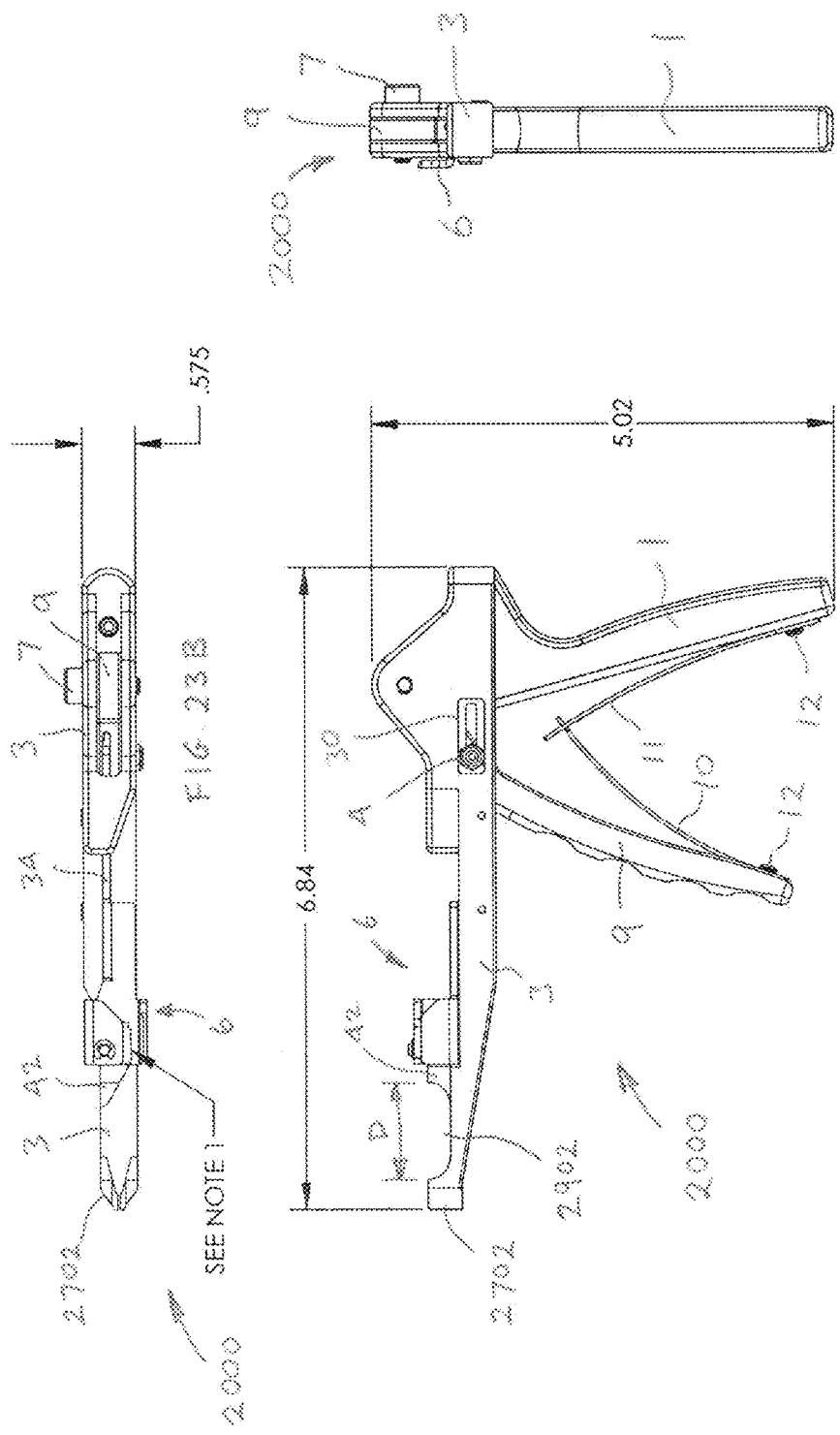

| ITEM NO. | PartNo | DESCRIPTION | QTY. |
|---|---|---|---|
| 1 | 20052 | HANDLE LEG | 1 |
| 2 | 20053 | PIN, .125 DIA x .375 LG | 1 |
| 3 | 20054 | MAIN BODY | 1 |
| 4 | 20055 | Nylon-Insert Hex Locknut | 1 |
| 5 | 20056 | SCREW, #4-40, .50 LG | 1 |
| 6 | 20050 | CARRIER SUB-ASM | 1 |
| 7 | 20057 | SCREW, .250 SHOULDER, #10-32 | 1 |
| 8 | 20058 | SCREW, .094 SHOULDER, #2-56 | 3 |
| 9 | 20059 | TRIGGER - CURVED | 1 |
| 10 | 20060 | LEAF SPRING - TRIGGER | 1 |
| 11 | 20061 | LEAF SPRING - HANDLE | 1 |
| 12 | 20062 | SCREW, #3-48 x .125 LG | 2 |
| 13 | 20063 | PIN, .0625 DIA x .250 LG | 1 |

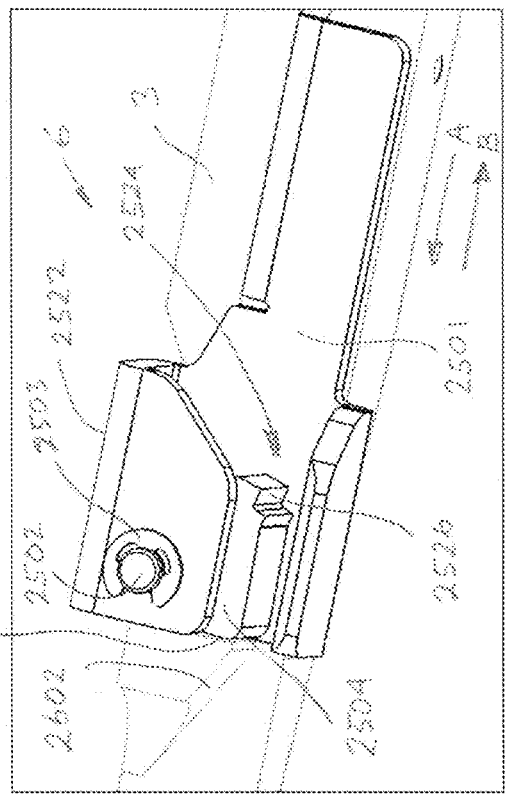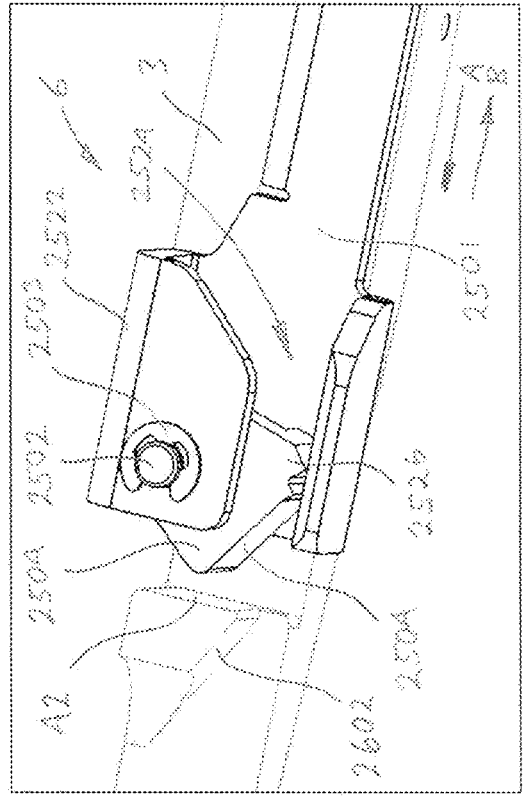

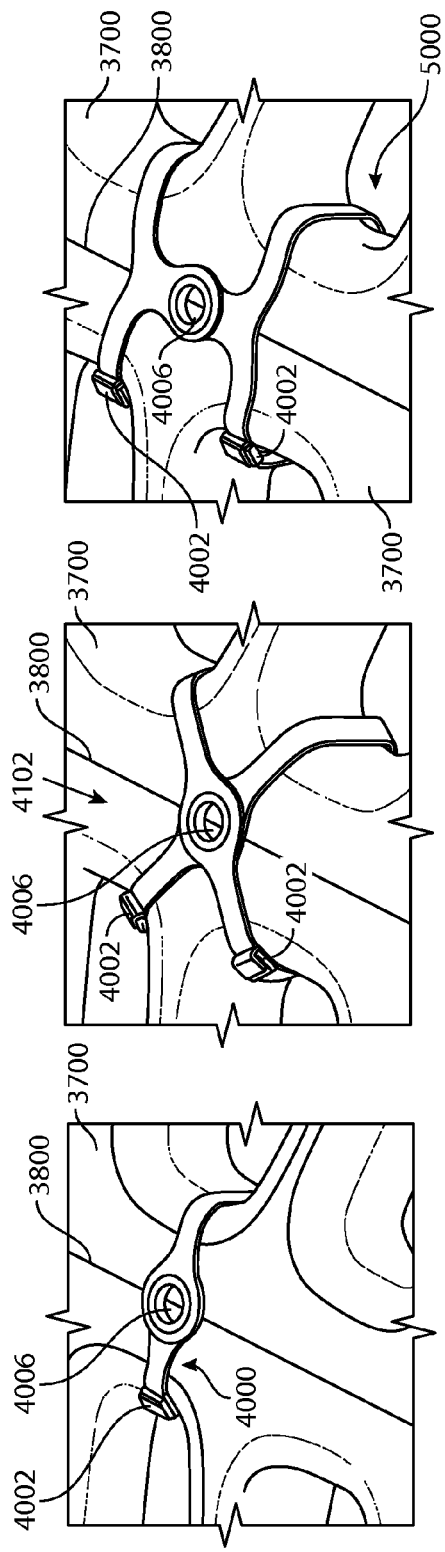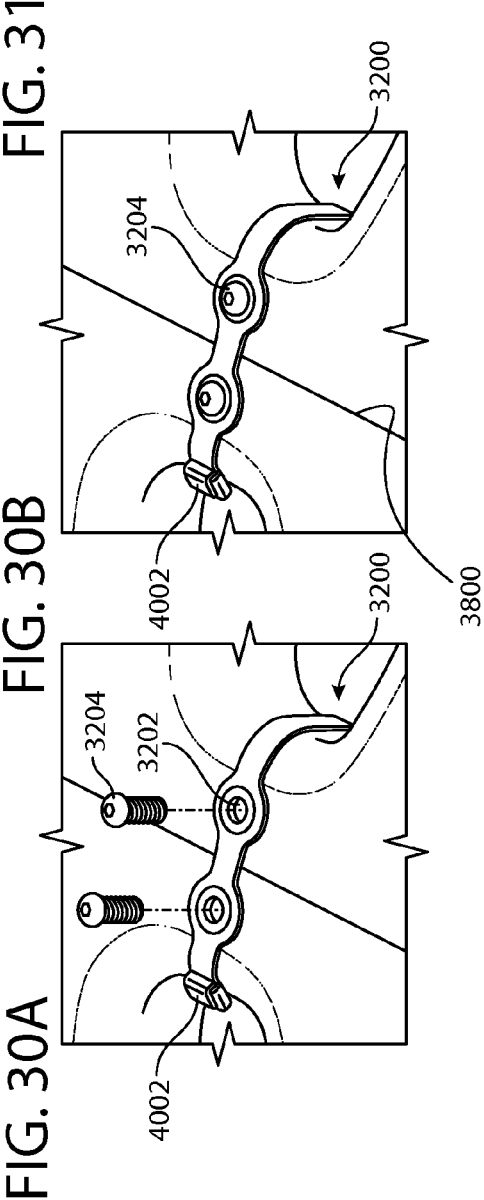

(Normally open (~2mm gap))

Dog clamps shut

Squeezing the trigger releases the dog (torsion spring biases the dog CCW direction) to engage the strap.

Carriage travel - .52"(13mm)

Lever - 3.5 : 1 mechanical advantage

Pin fixed to carriage... pin rides in lever spot

Return spring can achieve 7X the force

Loop Lever

Curved Lever

Curved Lever

Return spring can achieve 7X the force

Pin fixed to carriage... pin rides in lever spot

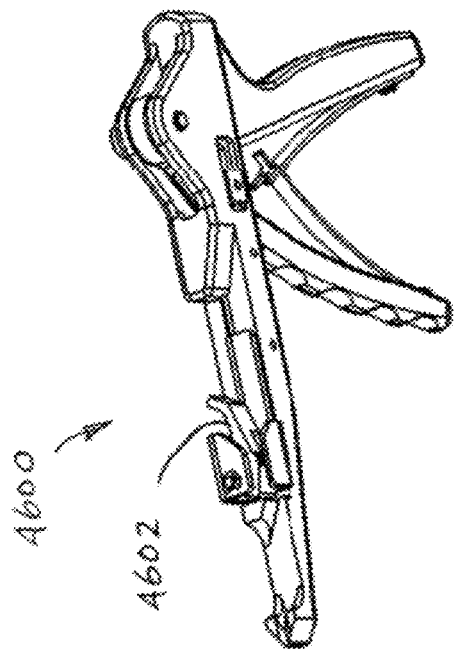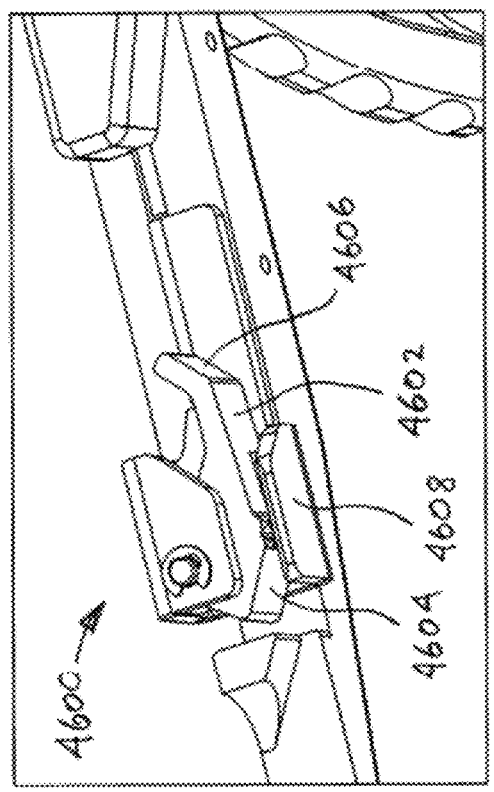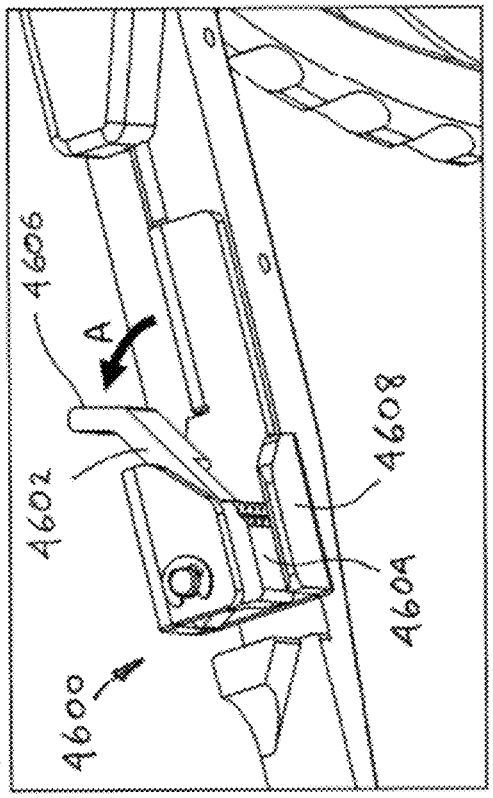

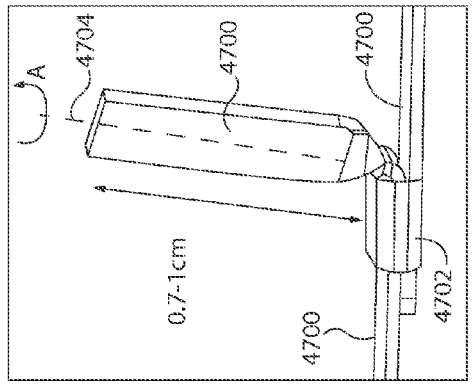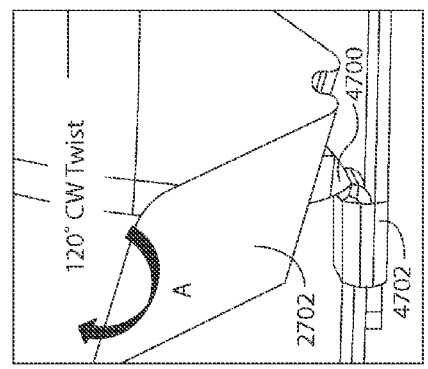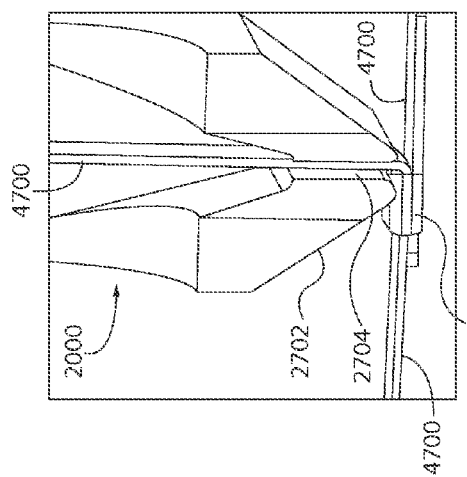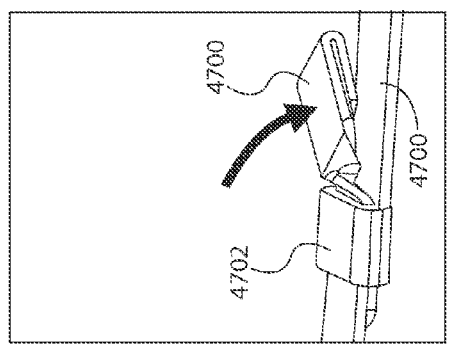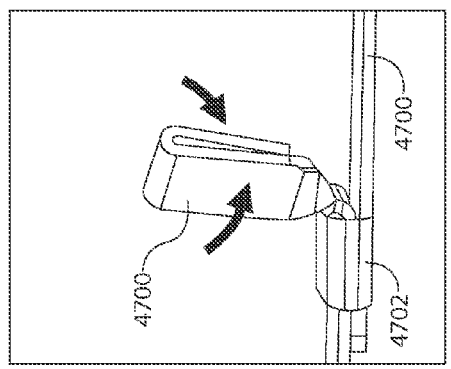

STERNUM BAND TENSIONER DEVICE, SYSTEM AND METHOD

CROSS REFERENCE TO RELATED APPLICATIONS

This application claims priority to U.S. Provisional Application No. 61/498,508, filed on Jun. 17, 2011, which is herein incorporated by reference in its entirety.

FIELD OF THE INVENTION

The present invention relates to tissue closure. More specifically, the disclosure relates to devices, systems and methods of connecting and closing portions of a sternum after a partial or full sternotomy.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

Conventional methods for sternum repair following surgery often involve extensive forces being applied, which may be difficult to apply and uncomfortable. For example, sternal repair following heart surgery typically uses steel wire which is passed between the ribs and twisted/crimped together to achieve stability between the bone edges.

For sternal reconstruction the wires are subject to stress forces caused by sternal movement from breathing. This leads to metal fatigue and fracturing. Wire integrity loss can cause sternal infection and non-union. This occurs in 5% of all open heart surgeries. Furthermore there have been reports of allergy to metals which often prompts the removal of wires and risk exposure by the patient. The wires are also dependent upon the skill of the surgeons as they tighten the wires. Too many turns in the wire may unnecessarily weaken the wire and subject it to future failure. Sternal plating systems have been developed, much like plates for fractured bones; however there are many hurtles in the success of the plates. They are cumbersome and difficult to apply, and the cardiothoracic surgeons are usually not trained or comfortable with the application. Typically, they are reserved for sternal dehiscence cases, and they are expensive.

Accordingly, there exists a need for improved systems and methods for sternum repair.

SUMMARY OF THE DISCLOSURE

According to some embodiments of the disclosure, a band tensioning device is provided with a main body, a handle, a trigger, a carrier, a dog and a spring. The main body has proximal and distal ends, a top side and a bottom side. The handle depends from the proximal end of the main body and is immovably affixed thereto. The trigger depends from the proximal end of the main body distal to the handle and is movably affixed to the main body. The carrier is movably coupled to the main body such that it moves proximally and distally along the main body. The carrier is linked to the trigger such that when the trigger is moved proximally toward the handle, the carrier is pulled proximally along the main body by the trigger. The carrier has a vertically extending surface accessible by a band inserted from the top side of the main body. The dog is pivotably mounted to the carrier and has a toothed engagement surface configured to pinch a smooth band between itself and the vertically extending surface of the carrier. The dog is configured to pivot between a closed position against a band or the vertically extending surface and an open position away from the vertically extending surface. The spring spans between the carrier and the dog to bias the dog towards the closed position. The distal end of the main body includes a vertically extending slot accessible by a band inserted from the top side of the main body such that a distal end of a band may be placed into the slot and between the dog and vertically extending surface of the carrier from the top side of the main body to tension the band.

In some embodiments, the distal end of the main body comprises vertically oriented angled surfaces symmetrically formed with respect to a central longitudinal axis of device. The angled surfaces may form an included angle of about 75 degrees, or an included angle of less than 75 degrees. The angled surfaces may include distal edges having a rounded profile to provide better engagement with a band buckle.

In some embodiments of the device, the dog includes a distally protruding portion configured to contact a carrier stop located on the main body to pivot the dog towards the open position. The dog may include an actuation lever configured to allow manual actuation of the dog towards the open position.

In some embodiments, the device comprises a single dog. In some embodiments, the device cannot cut a band placed therein. In some embodiments, the main body is configured to generally expose a band spanning between the vertically extending slot of the tip and the vertically extending surface of the carrier for better visibility of the band by a surgeon.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 5-9 show various embodiments of tissue closure devices having bands pivotably connected at mid-portions.

FIGS. 10-13 show various embodiments of tissue closure devices having bands pivotably connected at end-portions.

FIGS. 15A-15C show various embodiments of an H-shaped tissue closure device.

FIGS. 16A-16C show details of forming an exemplary buckle on the end of a band.

FIGS. 19A-19C show further details of a closure device with a curved needle formed on its distal end.

FIGS. 20-24 show various views of an exemplary band tensioning device constructed according to aspects of the invention.

FIG. 26A shows the carrier subassembly of FIG. 25 is a forward/distal position on a portion of the device shown in FIGS. 20-24.

FIG. 26B shows the carrier subassembly of FIG. 25 is a rearward/proximal position on a portion of the device shown in FIGS. 20-24.

FIG. 30A shows a single band closure device installed on a sternum.

FIG. 30B shows a double band closure device installed on a sternum.

FIG. 31 shows an H-shaped closure device installed on a sternum.

FIGS. 32A and 32B show an alternative closure device installed on a sternum.

FIGS. 46A-46C show another exemplary band tensioning device having a dog actuation lever.

FIGS. 47A-47E show another exemplary method for securing bands.

DETAILED DESCRIPTION

While various embodiments of the invention are shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

This application is related to U.S. application Ser. No. 12/888,357 filed Sep. 22, 2010, U.S. application Ser. No. 12/727,212 filed Mar. 18, 2010, U.S. Provisional Application No. 61/161,515 filed Mar. 19, 2009 and U.S. Provisional Application No. 61/252,145 filed Oct. 15, 2009. These applications disclose various closure tissue closure systems, primarily for use after a full or partial sternotomy. The tensioning instruments disclosed in the present application are configured to work with the tissue closure systems described in the above applications.

FIGS. 1A-1E show various exemplary embodiments of tissue connecting devices that may be used to close portions of a sternum after a sternotomy. FIG. 1F shows a cut feature that may be used with any of the embodiments shown in FIGS. 1A-1E. Each of the embodiments shown in FIGS. 1A-1E is integrally formed and may be constructed from a single piece of material. Each device is shown in the configuration it would take when implanted around a sternum, with bands inserted through the buckles, tensioned and distal ends cut off.

Figure 1:
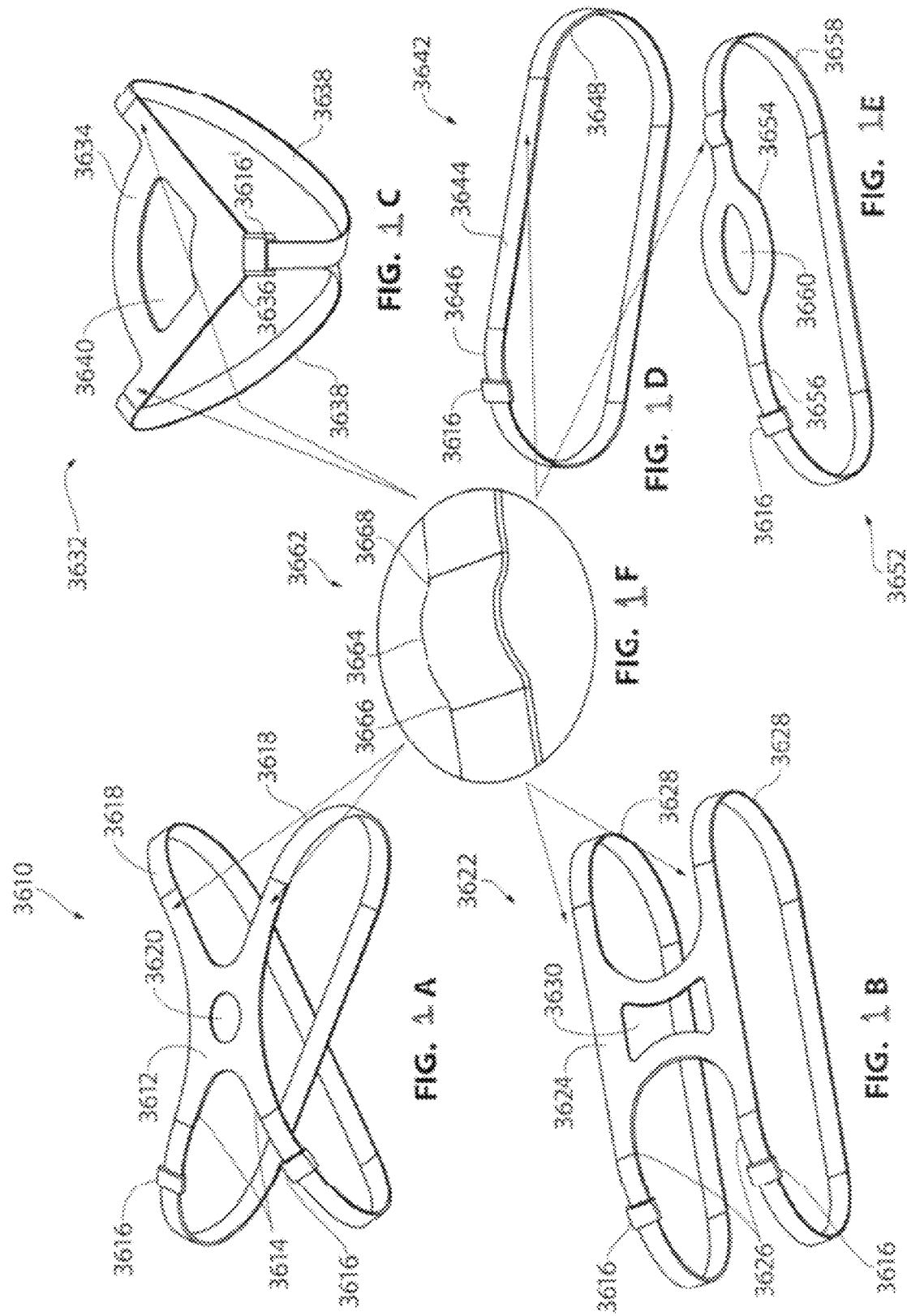
FIGS. 1A-1E show various embodiments of tissue closure devices.
FIG. 1F shows an offset feature that may be used with any of the tissue closure devices.

FIG. 1A shows an integrally formed tissue connecting device 3610. Device 3610 includes a central body 3612. In this embodiment, two straps 3614 are integrally formed with and extend from one end of central body 3612 at non-parallel angles. A buckle 3616 may be integrally formed on the distal end of each strap 3614, as will be subsequently described in more detail. On the opposite end of central body 3612, two bands 3618 are integrally formed with and extend from central body 3612 at non-parallel angles. Bands 3618 are configured to encircle a sternum and be received through buckles 3616.

In the embodiment shown in FIG. 1A, bands 3618 cross each other on the posterior side of the sternum and are received through the buckles 3616 that are diagonally opposite the central body 3612 from where the band 3618 takes off. In this configuration, the device forms an X shape and can be referred to as a "Figure 8". When device 3610 is installed on a sternum, straps 3614 may be located on opposite sides of a rib, or may be located between two ribs. Similarly, bands 3618 may be located on opposite sides of a rib, or may be located between two ribs. When straps 3614 and bands 3618 are located on opposite sides of a pair of laterally opposing ribs, such as depicted in FIG. 29A, device 3610 is generally better positioned to counteract cranial-caudal shear forces that occur between laterally opposite sides of the sternum. Straps 3614 and bands 3618 may also be positioned to encompass multiple pairs of laterally opposing ribs, as depicted in FIG. 29B.

Device 3610 may be provided with a circular view window 3620 through central body 3612 as shown. View window 3620 may be used by a surgeon to line up device 3610 during installation on a sternum. In particular, a cut line between two portions of a separated sternum or other tissue may be viewed through view window 3620. Device 3610 may then be centered over the cut line. Other view window configurations may be provided, such as oval, square, rectangular or other window shapes. The view window may be non-symmetrical. In some embodiments, multiple view windows are provided which may be separated by one or more structural portions.

Figure 36A:
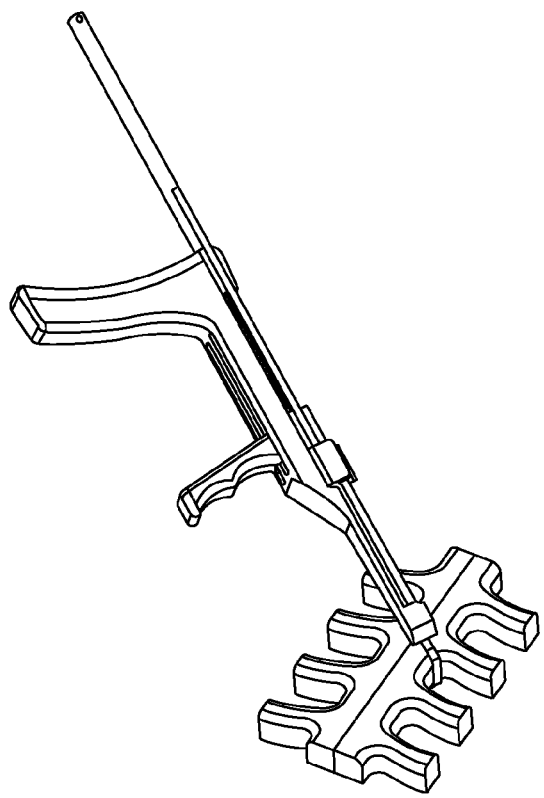
Figure 36B:
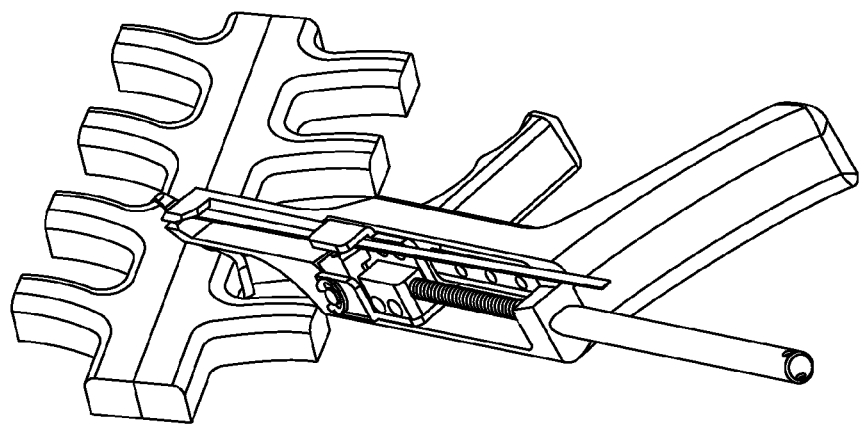
Figure 37A:
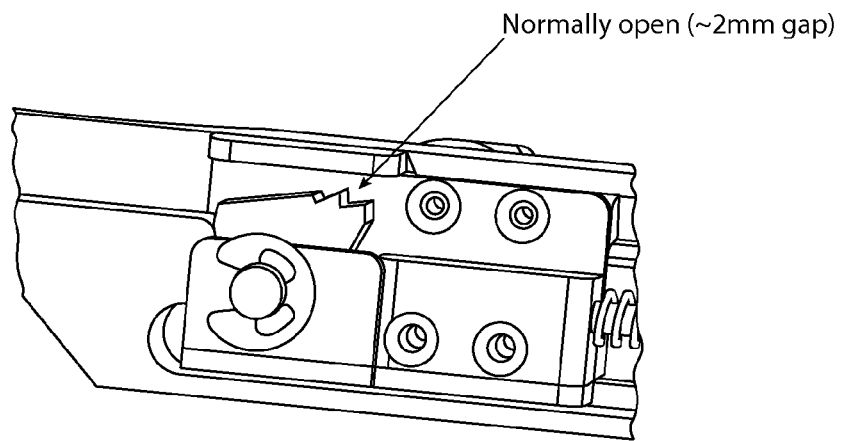
Figure 37B:
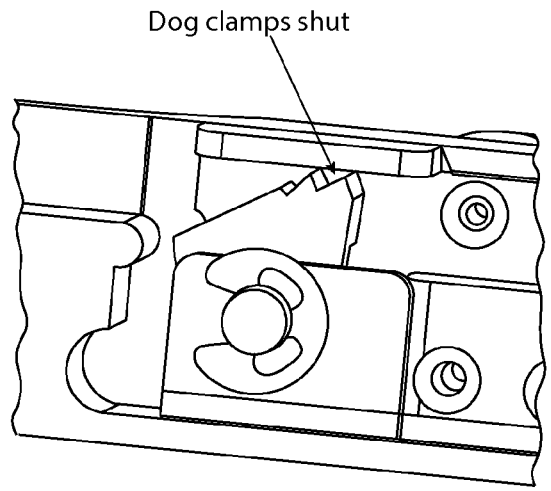
Figure 38:
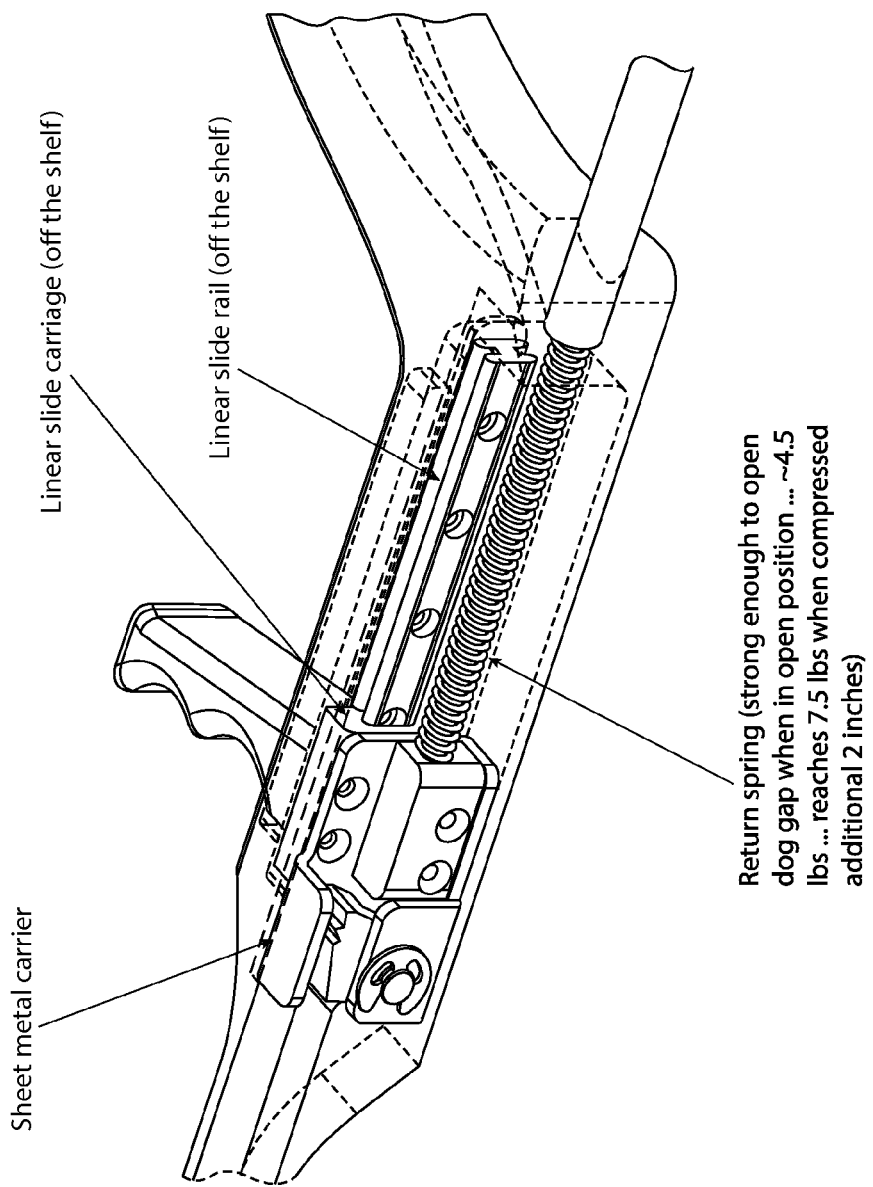
Figure 39B:
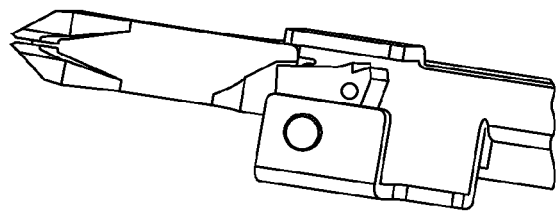
Figure 39A:
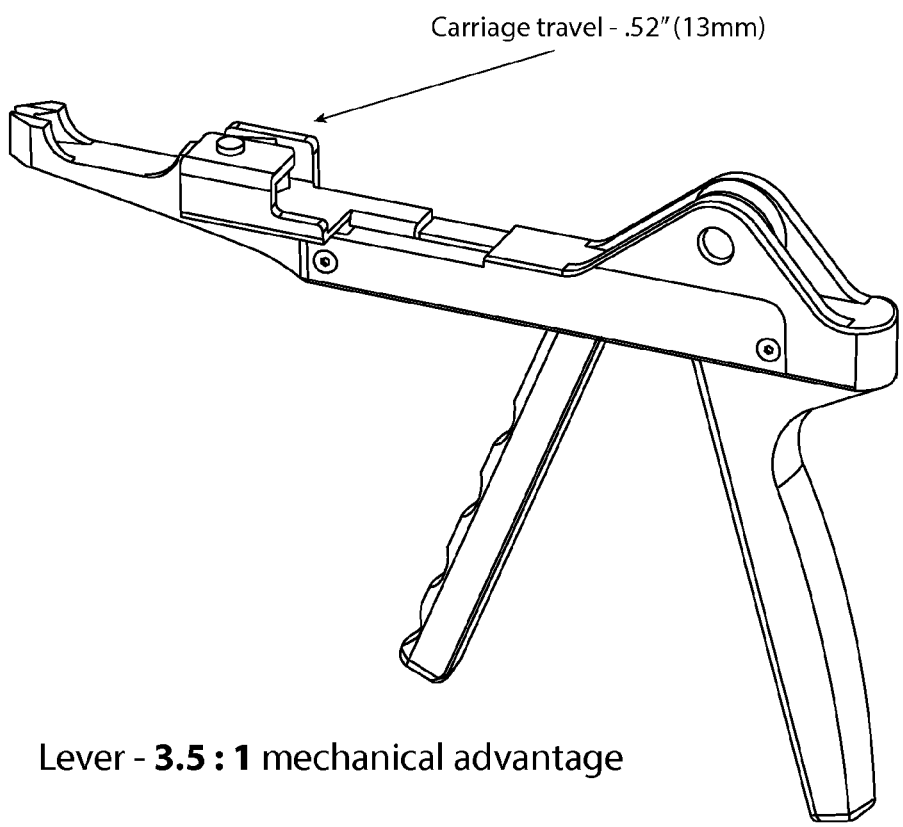
Figure 40B:
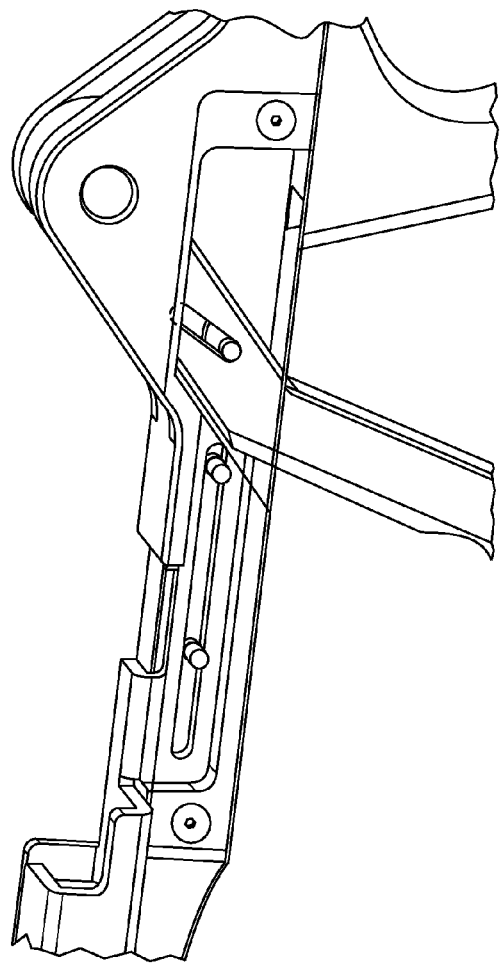
Figure 40D:
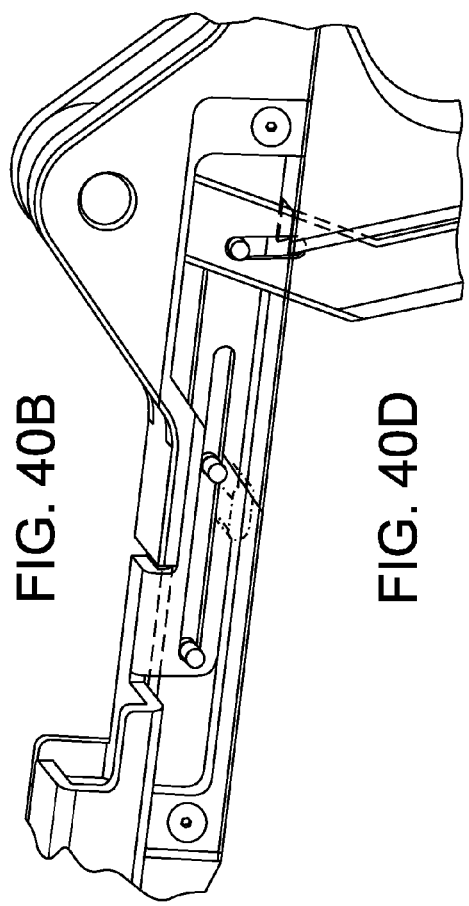
Figure 40A:
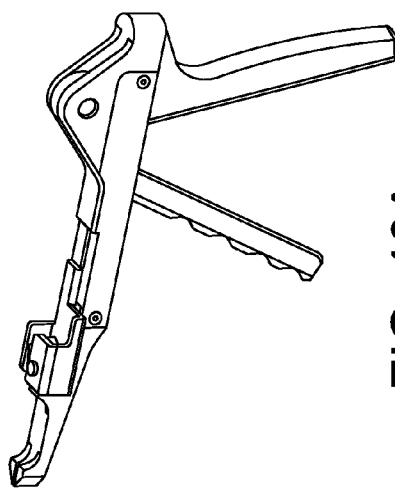
Figure 40C:
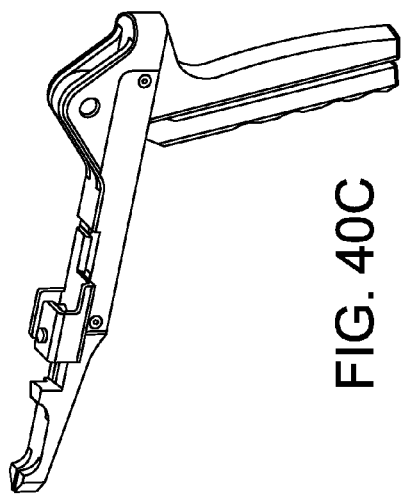
Figure 41A:
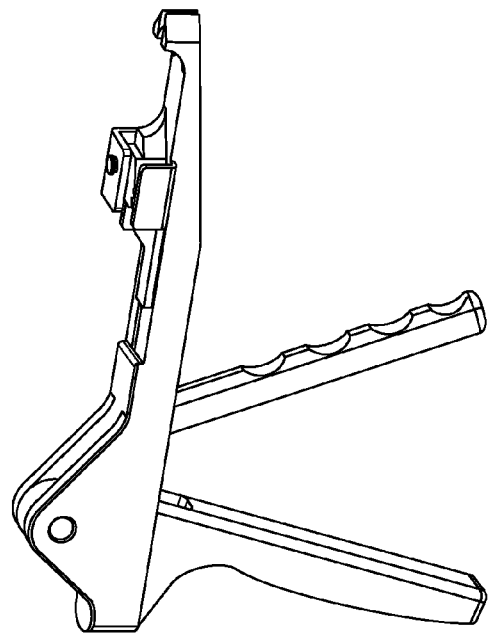
Figure 41B:
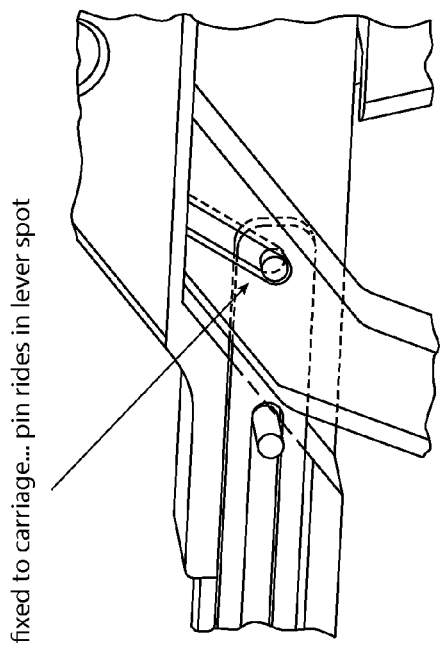
Figure 41C:
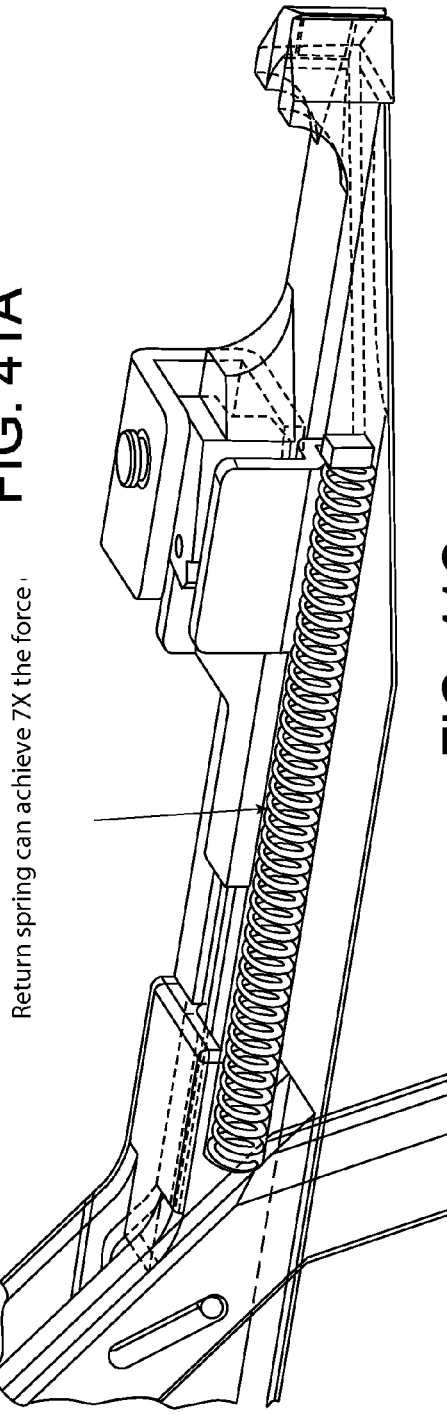
Figure 42A:
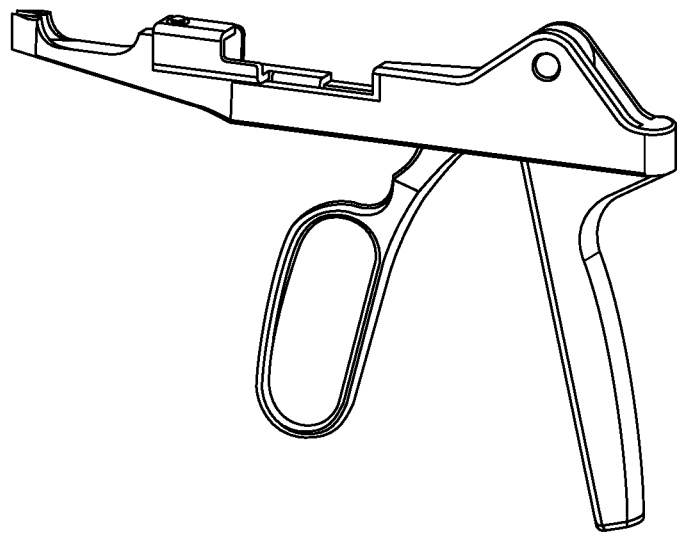
Figure 42B:
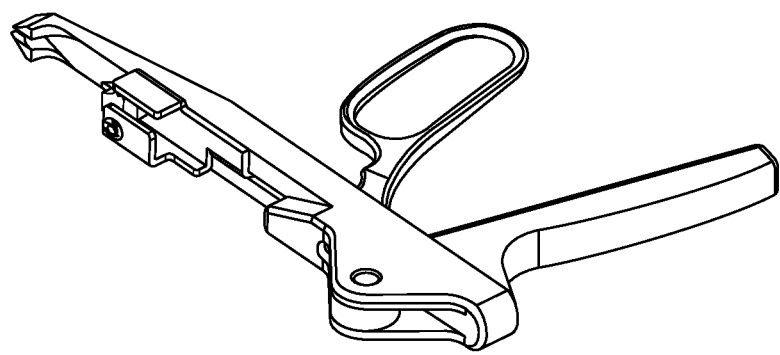
Figure 43A:
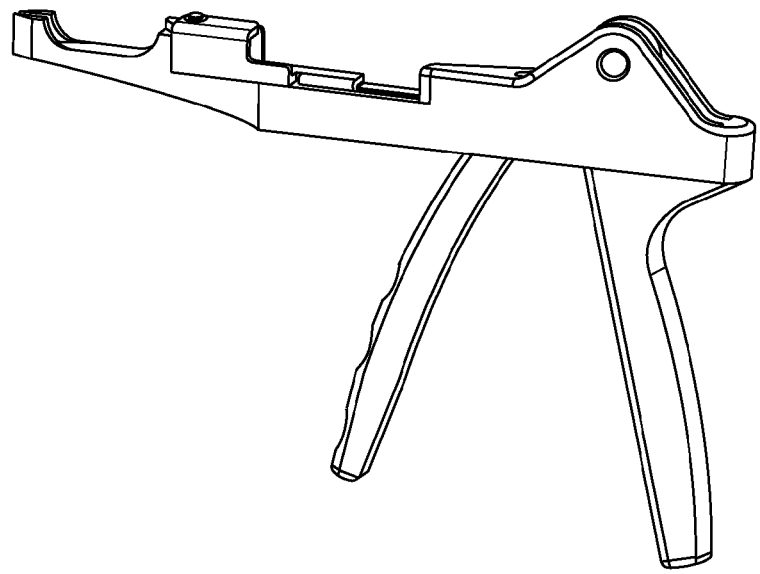
Figure 43B:
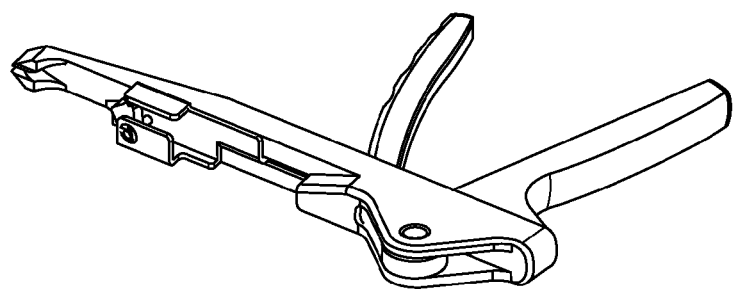
Figure 44A:
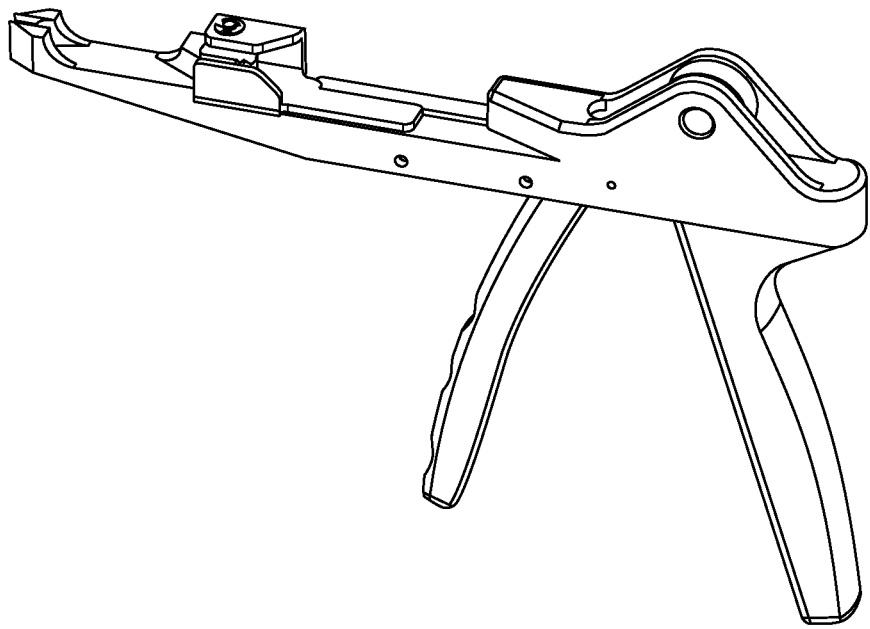
Figure 44B:
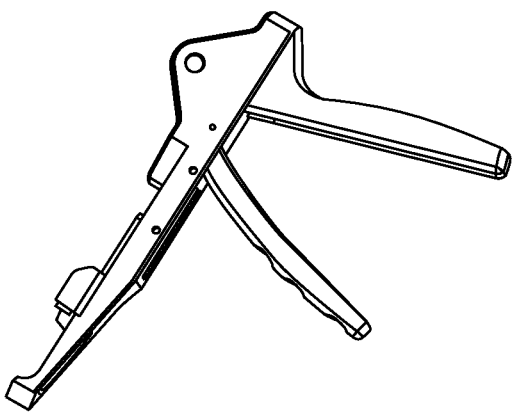
Figure 45A:
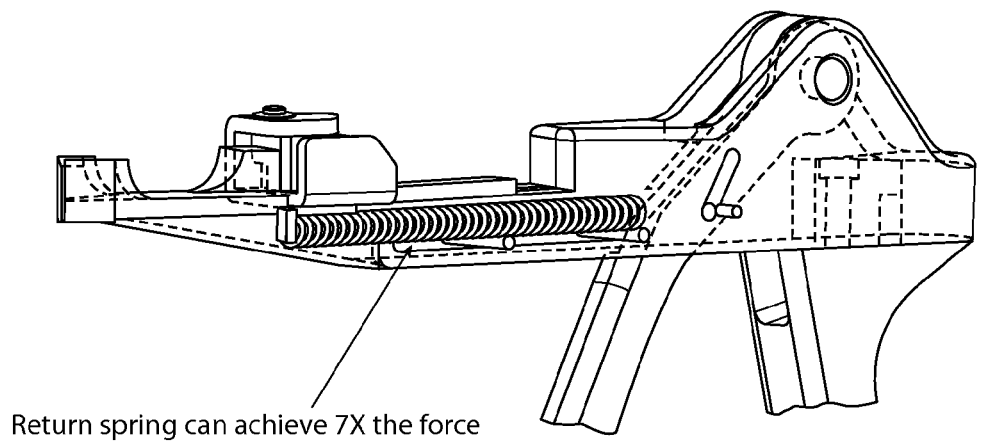
Figure 45B:
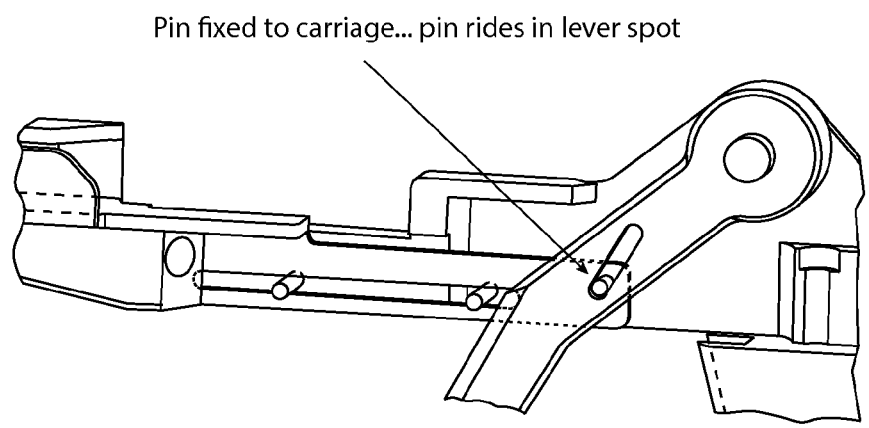

FIG. 36B shows another example of an integrally formed tissue connecting device 3622. Device 3622 includes a central body 3624. In this embodiment, two straps 3626 are integrally formed with and extend from one end of central body 3624 parallel to one another. A buckle 3616 may be integrally formed on the distal end of each strap 3626, as will be subsequently described in more detail. On the opposite end of central body 3624, two bands 3628 are integrally formed with and extend from central body 3624 parallel to one another. Bands 3628 are configured to encircle a sternum and be received through buckles 3616.

In the embodiment shown in FIG. 1B, bands 3628 remain parallel to each other as they pass around the posterior side of the sternum and are received through the buckles 3616 that are on the same side of central body 3624 from where the band 3628 takes off. In this configuration, the device forms an H shape and can be referred to as a "Figure H". When device 3622 is installed on a sternum, straps 3626 may be located on opposite sides of a rib, or may be located between two ribs. Similarly, bands 3628 may be located on opposite sides of a rib, or may be located between two ribs. When straps 3626 and bands 3628 are located on opposite sides of a pair of laterally opposing ribs, such as depicted in FIG. 29A, device 3622 is generally better positioned to counteract cranial-caudal shear forces that occur between laterally opposite sides of the sternum. Straps 3626 and bands 3628 may also be positioned to encompass multiple pairs of laterally opposing ribs, as depicted in FIG. 29B.

Device 3622 may be provided with an hourglass shaped view window 3630 through central body 3624 as shown. View window 3630 may be used by a surgeon to line up device 3622 during installation on a sternum. In particular, a cut line between two portions of a separated sternum or other tissue may be viewed through view window 3630. Device 3622 may then be centered over the cut line. Other view window configurations may be provided, such as oval, square, rectangular or other window shapes. The view window may be non-symmetrical. In some embodiments, multiple view windows are provided which may be separated by one or more structural portions.

FIG. 1C shows another example of an integrally formed tissue connecting device 3632. Device 3632 includes a central body 3634. In this embodiment, a strap 3636 is integrally formed with and extends from one end of central body 3634. A buckle 3616' may be integrally formed on strap 3636, as will be subsequently described in more detail. On the opposite end of central body 3634, two bands 3638 are integrally formed with and extend from central body 3634 at a non-parallel angle to each other. Bands 3638 are configured to encircle portions of a sternum and may both be received through a single buckle 3616'.

In the embodiment shown in FIG. 1C, bands 3638 diverge from each other at one end of central body 3634 and converge at the opposite end of central body 3634. In this configuration, the device forms a Y shape and can be referred to as a "Figure Y". Device 3632 may be used to reconnect two or more portions of a sternum after a partial sternotomy, as will be subsequently described in relation to FIG. 4. In such a procedure, bands 3638 may pass through holes formed in the sternum rather than passing around the periphery of the sternum.

Device 3632 may be provided with a curved, trapezoidal view window 3640 through central body 3634 as shown. View window 3640 may be used by a surgeon to line up device 3632 during installation on a sternum. In particular, a cut line between two portions of a separated sternum or other tissue may be viewed through view window 3640. Device 3632 may then be centered over the cut line. Other view window configurations may be provided, such as oval, square, rectangular or other window shapes. The view window may be non-symmetrical. In some embodiments, multiple view windows are provided which may be separated by one or more structural portions.

FIG. 1D shows another example of an integrally formed tissue connecting device 3642. Device 3642 includes a central body 3644. In this embodiment, a strap 3646 is integrally formed with and extends from one end of central body 3644. A buckle 3616 may be integrally formed on the distal end of strap 3646, as will be subsequently described in more detail. On the opposite end of central body 3644, a band 3648 is integrally formed with and extends from central body 3644. Band 3648 is configured to encircle a sternum and be received through buckle 3616. In this embodiment, strap 3646, central body 3644 and band 3648 are essentially a single band that may have a constant width and thickness.

FIG. 1E shows another example of an integrally formed tissue connecting device 3652. Device 3652 includes a central body 3654. In this embodiment, a strap 3656 is integrally formed with and extends from one end of central body 3654. A buckle 3616 may be integrally formed on the distal end of strap 3656, as will be subsequently described in more detail. On the opposite end of central body 3654, a band 3658 is integrally formed with and extends from central body 3654. Band 3658 is configured to encircle a sternum and be received through buckle 3616.

Device 3652 may be provided with an oval shaped view window 3660 through central body 3654 as shown. View window 3660 may be used by a surgeon to line up device 3652 during installation on a sternum. In particular, a cut line between two portions of a separated sternum or other tissue may be viewed through view window 3660. Device 3652 may then be centered over the cut line. Other view window configurations may be provided, such as circular, square, rectangular or other window shapes. The view window may be non-symmetrical. In some embodiments, multiple view windows are provided which may be separated by one or more structural portions.

FIG. 1F shows an offset feature 3662 that may be used in any of the devices shown in FIGS. 1A-1E or any of the devices described herein. In the example shown in FIG. 1F, offset feature 3662 is created in a band, strap or central body portion by forming an arcuate portion 3664 between two bend lines 3666 and 3668. This arrangement causes arcuate portion 3664 to be raised above the adjacent device portions, leaving a gap between arcuate portion 3664 and underlying tissue. The gap may be used to allow a portion of a cutting instrument to be placed between the device and a sternum or other underlying tissue, thereby allowing the band, strap or central body portion to be more easily cut with the cutting instrument. Cutting and removing the device may be needed when it is desired to reposition or replace the device, remove the device after tissue healing, or during a later planned or emergency procedure.

In some embodiments, offset feature 3662 may be configured to provide the device with a more resilient spring force. For example, when a patient coughs, rolls on his side in bed, or otherwise puts an increased momentary force on the closure device, the material of a traditional closure device may exceed its yield strength and elongate, bite into the underlying tissue, or its position may slip. Such activity can cause traditional closure devices such as wire to break or become loose. Offset feature 3662 on the other hand can allow the closure device to momentarily expand to accommodate the extra force, and then resume its desired size and the load it places on the underlying tissue. Such resiliency can also allow the device to maintain the desired amount of pressure on the underlying tissue despite "tissue creep" that can occur during healing.

In some embodiments, a single offset feature 3662 may be used on the device, or multi offset features may be used. Multiple offset features may be placed side by side and/or on opposite sides of the device. The shape of the offset feature may be arcuate as shown, or an inverted U, inverted V, square, rectangle, triangle, inverted triangle, Z-shape, omega, or other shape or combination of shapes. The arcuate shape shown in FIG. 1F has the advantages of being low profile, and with no sharp features to disrupt adjacent tissue.

As shown in FIGS. 1A, 1B, 1D and 1E, each of the closure devices may be configured so that the buckle or buckles 3616 are located at least partially on a lateral side of the sternum, rather than on the anterior face of the sternum. This arrangement keeps the buckles from protruding outward toward the patient's skin, which can cause irritation and/or tissue damage as the skin is pressed against the device and/or moves laterally relative to the device. In some embodiments, a strap connecting a buckle to a central body may be relatively long, as shown in FIGS. 1A, 1B, 1D and 1E, may be short as shown in FIG. 1C, or may be non-existent with the buckle built directly into the central body.

Before being implanted, the devices shown in FIGS. 1A-1E may be provided with straight or curved delivery needles (not shown in these figures) mounted on the ends of each band, as will be subsequently described in further detail. After being used to thread the bands through and/or around the desired tissue, these needles may then be cut off.

Figure 2:
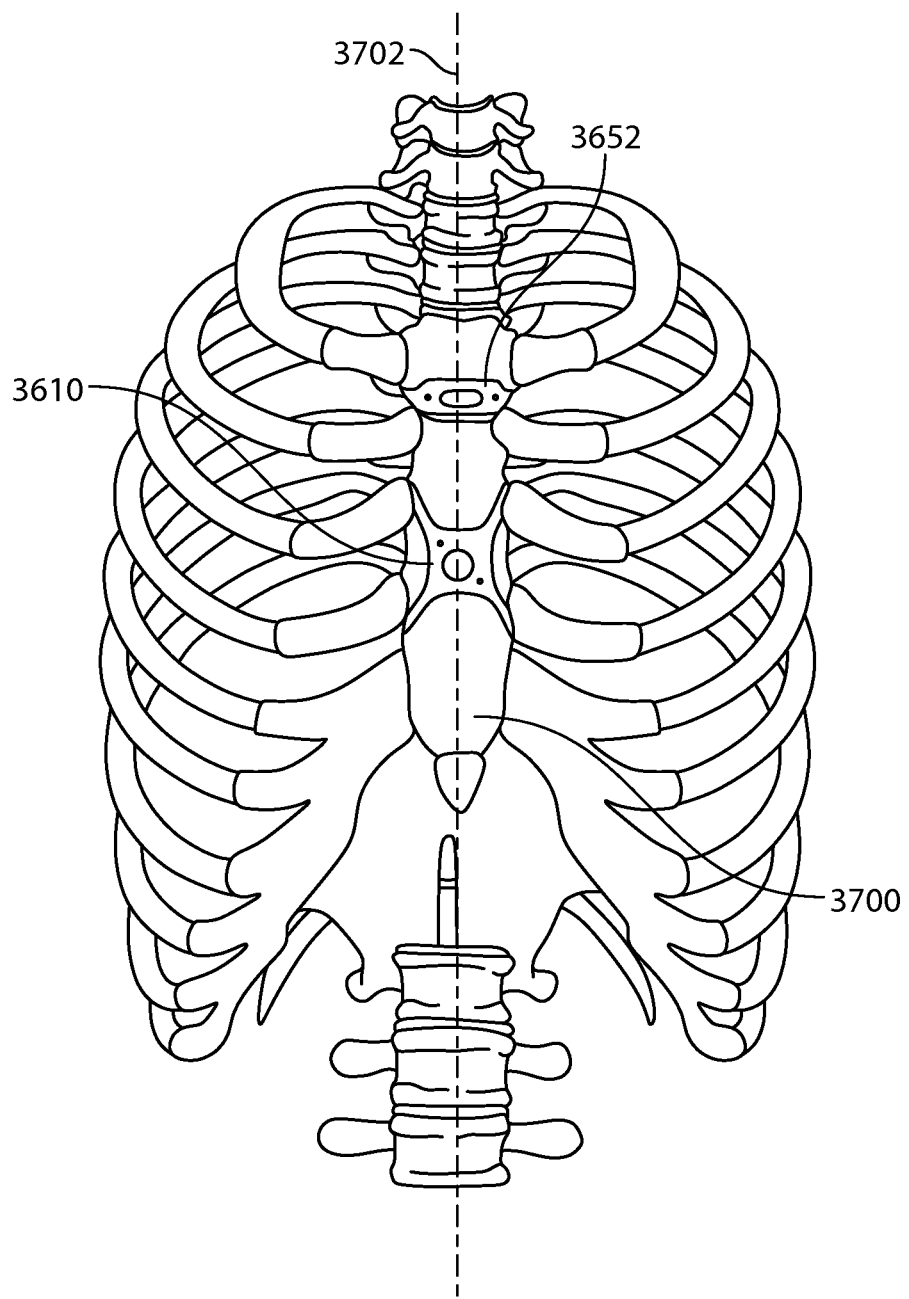
FIG. 2 shows two different tissue closure devices used to close portions of a sternum after a full sternotomy.

FIG. 2 shows a "Figure 8" device 3610 and a single band device 3652 implanted around a sternum 3700. A full sternotomy cut line 3702 is depicted by a dotted line running down the midline of sternum 3700. Depending on the particular procedure, a single device may be used to close the sternum, or multiple devices may be used. A single type of device among those shown in FIGS. 1A-1E may be used, or a combination of different devices may be used.

Figure 3:
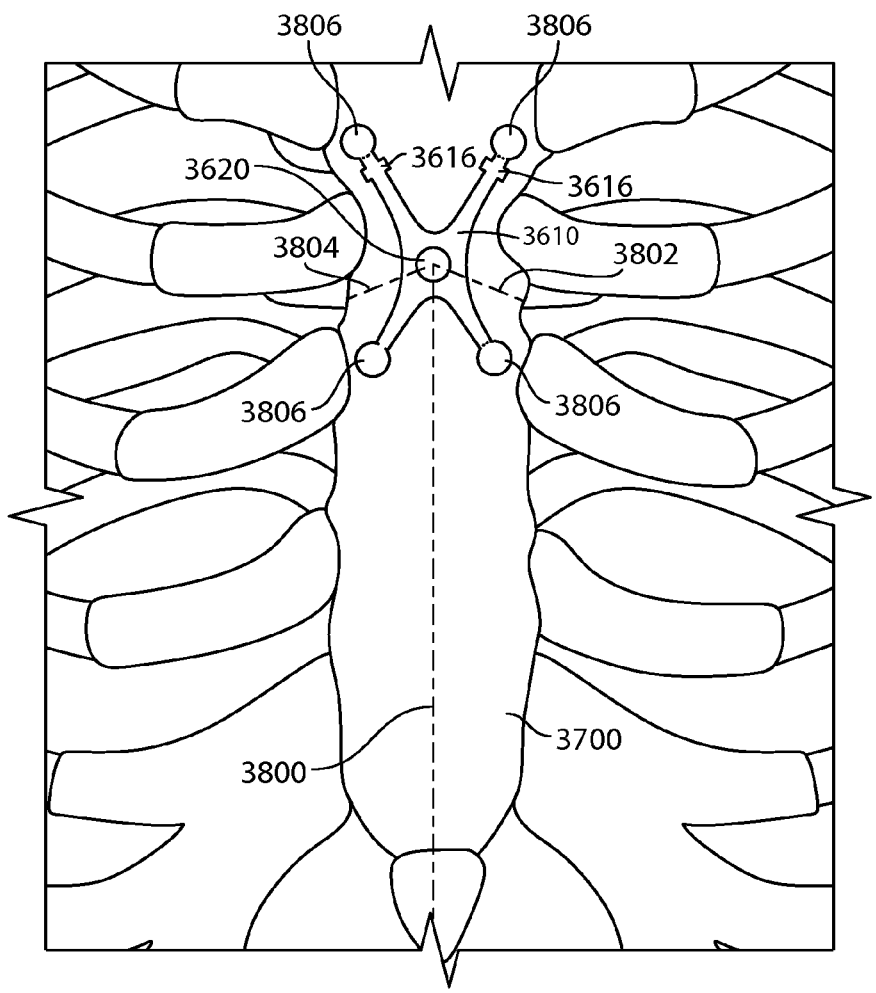
FIG. 3 shows a tissue closure device used to close portions of a sternum after a partial sternotomy.
Figure 4:
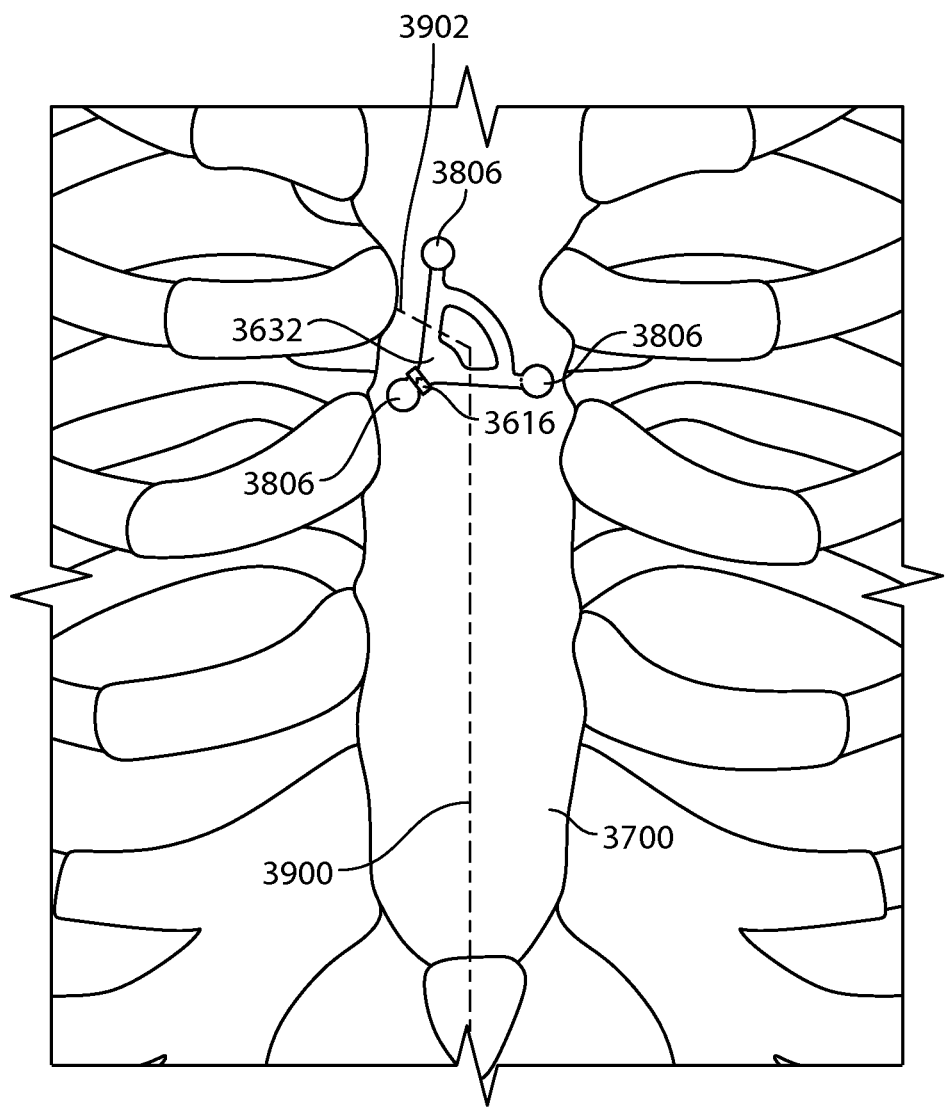
FIG. 4 shows a tissue closure device used to close portions of a sternum after a partial sternotomy.

FIGS. 3 and 4 show examples of the inventive closure devices being used for partial sternotomies. In FIG. 3, a first type of partial sternotomy may be performed by making a first cut line 3800 along the mid-line of the sternum 3700 as shown, but not extending the cut all the way through the cranial end of the sternum. A second cut 3802 may be made from a left lateral extent of the sternum 3700 at a medial-cranial angle to the cranial end of the first cut 3800, as shown. A third cut 3804 may be made from a right lateral extent of the sternum 3700 at a medial-cranial angle to the cranial end of the first cut 3800, as shown. The three cuts 3800, 3802 and 3804 do not necessarily need to be made in any particular order or direction. The left and right portions of sternum 3700 may then be separated to access underlying tissue and organs, such as during cardiac surgery.

To close the sternum after the above-described partial sternotomy, four holes 3806 may be drilled through the portions of the sternum as shown in FIG. 3. A drill guide or template may be placed over sternum 3700 to aid the surgeon in locating proper positions for holes 3806. The distal ends of bands 3618 of Figure 8 device 3610 (shown in FIG. 1A) may each be threaded through one of the lower holes 3806 in sternum 3700. Bands 3618 may then each be threaded diagonally across the posterior side of sternum 3700 and up through one of the upper holes 3806. To facilitate this process, a curved needle may be attached or formed on the distal end of each band 3618, as will be subsequently described in more detail. Once the bands 3618 have been threaded through holes 3806, the needles may be cut off and bands 3618 may be threaded through buckles 3616. Bands 3618 may then be properly tensioned and excess lengths cut off, leaving the three portions of sternum 3700 properly secured for healing by device 3610 as shown in FIG. 3. It should be noted that view window 3620 of device 3610 is positioned over the intersection of cut lines 3800, 3802 and 3804.

FIG. 4 depicts a second type of partial sternotomy that may be closed with a Figure Y device 3632. This second type of partial sternotomy may be performed by making a first cut line 3900 along the mid-line of the sternum 3700 as shown, but not extending the cut all the way through the cranial end of the sternum. A second cut 3902 may be made from a right (or left) lateral extent of the sternum 3700 at a medial-caudal angle to the cranial end of the first cut 3900, as shown. The two cuts 3900 and 3902 do not necessarily need to be made in any particular order or direction. The right portion of sternum 3700 (shown on the left in FIG. 4) may then be separated from the remainder of the sternum to access underlying tissue and organs, such as during cardiac surgery.

To close the sternum after the above-described partial sternotomy, three holes 3806 may be drilled through the portions of the sternum as shown in FIG. 4. A drill guide or template may be placed over sternum 3700 to aid the surgeon in locating proper positions for holes 3806. The distal ends of bands 3638 of Figure Y device 3632 (shown in FIG. 1C) may each be threaded through one of the upper holes 3806 in sternum 3700. Bands 3638 may then each be threaded across the posterior side of sternum 3700 and up through the lowermost hole 3806. To facilitate this process, a curved needle may be attached or formed on the distal end of each band 3638, as will be subsequently described in more detail. Once the bands 3638 have been threaded through holes 3806, the needles may be cut off and bands 3638 may be threaded through the single buckle 3616. Bands 3638 may then be properly tensioned and excess lengths cut off, leaving the two portions of sternum 3700 properly secured for healing by device 3632 as shown in FIG. 4. It should be noted that view window 3640 of device 3632 is positioned over the intersection of cut lines 3900 and 3902.

Figure 7:
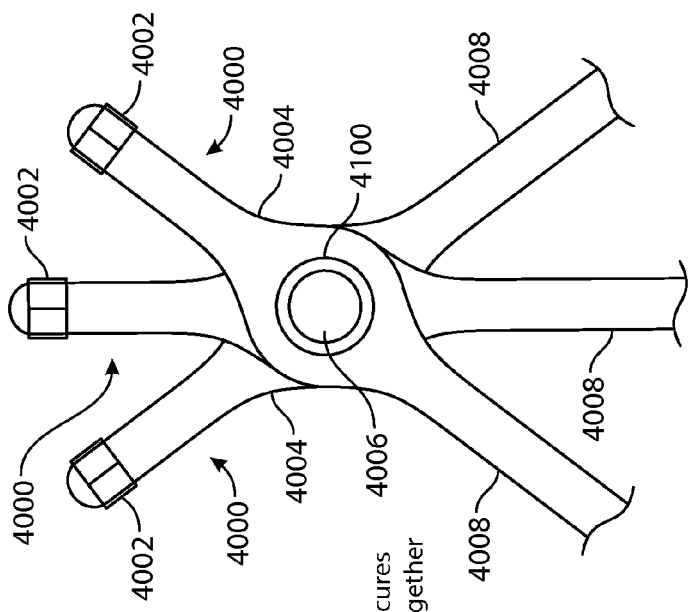
Figure 6:
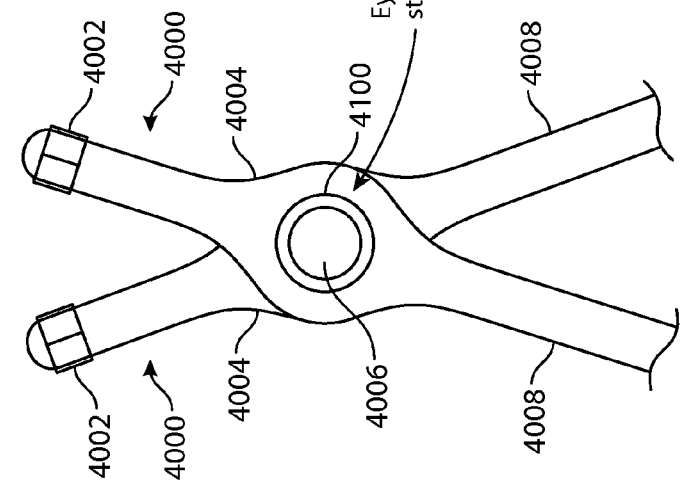
Figure 5:
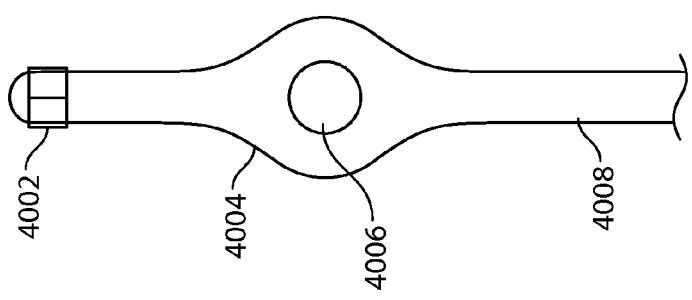

FIGS. 5-50 show additional closure device embodiments. These embodiments incorporate bands that may be pivoted relative to one another. Referring first to FIGS. 5-7, these embodiments can utilize a modular construction. FIG. 5 shows a portion of a single band 4000. Band 4000 includes a buckle 4002 at its proximal end, an enlarged mid-portion 4004 having a circular aperture 4006 there-through, and an elongated distal end portion 4008. Band 4000 may be used as a closure device by itself, similar to device 3652 shown in FIG. 1E, or it may be coupled with other band(s), as will now be described.

FIG. 6 shows two bands 4000, one positioned over the other, with their circular apertures 4006 aligned. Bands 4000 may be secured together at their mid-portions 4004 by an eyelet 4100 placed through the aperture 4006 of each band 4000. Eyelet 4100 keeps bands 4000 from separating, but allows them to pivot relative to one another about the center point of their aligned apertures 4006. Details of an exemplary eyelet 4100 are subsequently described relative to FIGS. 14A-14C. With bands 4000 pivotably coupled together at their mid-portions, closure device 4102 may be pivotably adjusted during installation to more closely adapt to the particular anatomy of the patient it is being implanted in. Eyelet 4100 may be fixed relative to the rotational position of one of the bands 4000, or both bands 4000 may pivot about eyelet 4100.

When implanted, two-band device 4102 may be secured around portions of a sternum, as with the previously described devices. The distal end portion 4008 of each band 4000 may be fastened to the buckle 4002 on the same band 4000 such that bands 4000 cross over each other on the posterior side of the sternum. Alternatively, the distal end portions 4008 may be fastened to the buckles 4002 on the opposite band 4000 such that bands 4000 remain generally parallel to one another on the posterior side of the sternum.

FIG. 7 shows three bands 4000 pivotably coupled at their mid-portions 4004 by eyelet 4100 to form closure device 4200. Like device 4102 shown in FIG. 6 and described above, device 4200 is pivotably adjustable and provides three bands for securing multiple tissue portions, such as portions of a sternum after a sternotomy. Eyelet 4100 may be fixed relative to the rotational position of one of the bands 4000, or all three bands 4000 may pivot about eyelet 4100.

When implanted, three-band device 4200 may be secured around portions of a sternum, as with the previously described devices. The distal end portion 4008 of each band 4000 may be fastened to the buckle 4002 on the same band 4000 such all three bands 4000 cross over each other on the posterior side of the sternum. Alternatively, the distal end portions 4008 of the outer pair of bands may be fastened to the buckles 4002 on the opposite band 4000, and the center band may connect to itself, such that all three bands 4000 remain generally parallel to one another on the posterior side of the sternum. Other fastening combinations may be used, such as the distal portion 4008 of each of the three bands 4000 connecting to the buckle 4002 of a different band.

As shown in FIGS. 5-7 and described above, one, two or three bands 4000 may be used as a tissue closure device, with the multiple band embodiments of FIGS. 6 and 7 providing pivotable coupling between mid-portions 4004 of the bands 4000. In other embodiments (not shown), more than three bands 4000 may be pivotably coupled together in a similar manner. Different devices, such as the single-band, double-band, and/or triple-band devices shown in FIGS. 5, 6 and 7, respectively, may be used together at different locations along a single sternum. It should be noted that a view window as previously described exists through the aperture(s) 4006 and/or eyelet 4100 in each of the exemplary embodiments shown in FIGS. 5-7. In other embodiments, a view window may be omitted, such as by using a solid eyelet.

FIGS. 8 and 9 show perspective views of a double-band device 4300 similar to device 4102 shown in FIG. 6. Device 4300 includes offset features 4302 on each of the bands 4000. Offset features 4302 have a rectangular profile and may provide cutting and/or spring functionality, as previously described in relation to offset feature 3662 shown in FIG. 1F. Offset features 4302 can also serve to limit pivoting movement. FIG. 8 shows bands 4000 pivoted such that offset features 4302 are moved apart. FIG. 9 shows bands 4000 pivoted such that offset features 4302 are moved into contact with one another. Further pivoting in this direction may be prevented by offset features 4302 contacting each other and stopping one band 4000 from passing over the other.

FIGS. 10-13 show further embodiments of closure devices that utilize a modular construction. FIG. 10 shows an exploded view of two band components 4500 and 4502 that can be pivotably coupled together to form closure device 4504. Band component 4500 has two end portions and a mid-portion. A buckle 4002 is formed on one of the end portions. The other end portion of band component 4500 is enlarged and has an aperture 4006 there-through. The mid-portion of band component 4500 is a slender band. In other embodiments (not shown), the mid-portion of band component 4500 can be very short or non-existent, with buckle 4002 directly coupled to the enlarged end portion of band component 4500.

Band component 4502 also has an enlarged end portion with an aperture 4006 there-through. Only part of the mid-portion of band component 4502 of this embodiment is shown in the figures due to its long length. The mid-portion may extend to the opposite end portion (not shown) as a band having a constant cross-section. A delivery needle may be attached or formed on the opposite end portion, as will be subsequently described in detail.

The right side of FIG. 10 shows the two bands 4500 and 4502, one positioned over the other, with their circular apertures 4006 aligned. Bands 4500 and 4502 may be secured together at their end-portions by an eyelet 4100 placed through the aperture 4006 of each band. Eyelet 4100 keeps bands 4500 and 4502 from separating, but allows them to pivot relative to one another about the center point of their aligned apertures 4006. Details of an exemplary eyelet 4100 are subsequently described relative to FIGS. 14A-14C. With bands 4500 and 4502 pivotably coupled together at their end-portions, closure device 4504 may be pivotably adjusted during installation to more closely adapt to the particular anatomy of the patient it is being implanted in. Eyelet 4100 may be fixed relative to the rotational position of one of the bands 4500 or 4502, or both bands may pivot about eyelet 4100.

When implanted, modular closure device 4504 may be secured around portions of a sternum, as with the previously described devices, with the distal end portion (not shown) of band 4502 fastened to the buckle 4002 of band 4500.

FIG. 11 shows another exemplary modular closure device 4600. Device 4600 is similar to device 4504 shown in FIG. 10, but includes an additional band 4502. In other words, device 4600 is formed from one band 4500 having a single buckle 4002, two bands 4502, and an eyelet 4100 passing through all three bands. In this embodiment, all three bands are pivotably coupled together at their end portions. Eyelet 4100 may be fixed relative to the rotational position of one of the bands, or all three bands may pivot about eyelet 4100. Buckle 4002 is configured to receive the end portions (not shown) of both bands 4502.

FIGS. 12 and 13 show another exemplary modular closure device 4700. Device 4700 is similar to device 4600 shown in FIG. 11, but includes an additional band 4500. In other words, device 4700 is formed from two bands 4500, each having a buckle 4002, two bands 4502, and an eyelet 4100 passing through all four bands. In this embodiment, all four bands are pivotably coupled together at their end portions. Eyelet 4100 may be fixed relative to the rotational position of one of the bands, or all four bands may pivot about eyelet 4100. Buckles 4002 are each configured to receive an end portions (not shown) of one of the two bands 4502.

When implanted, device 4700 may be secured around portions of a sternum, as with the previously described devices. The distal end portion of each band 4502 may be fastened to the buckle 4002 on the diagonally opposite side of the device such that bands 4502 cross over each other on the posterior side of the sternum. Alternatively, the distal end portions of bands 4502 may be fastened to the buckles 4002 on the same side of the device such that bands 4502 remain generally parallel to one another on the posterior side of the sternum.

As shown in FIGS. 10-13 and described above, one, two, three or four bands may be used as a tissue closure device, with the multiple band embodiments providing pivotable coupling between end portions of the bands 4500 and 4502. In other embodiments (not shown), more than four bands may be pivotably coupled together in a similar manner. Other combinations may be formed by coupling some bands at their mid-portions and other bands at their end portions to form a single device. Different devices, such as the double-band, triple-band and/or quadruple-band devices shown in FIGS. 10, 11 and 12-13, respectively, and/or the devices of FIGS. 5-9, may be used together at different locations along a single sternum. It should be noted that a view window as previously described exists through the apertures 4006 and eyelet 4100 in each of the exemplary embodiments shown in FIGS. 10-13. In other embodiments, a view window may be omitted, such as by using a solid eyelet. Offset features such as those previously described may be incorporated into these embodiments.

Figure 14A:
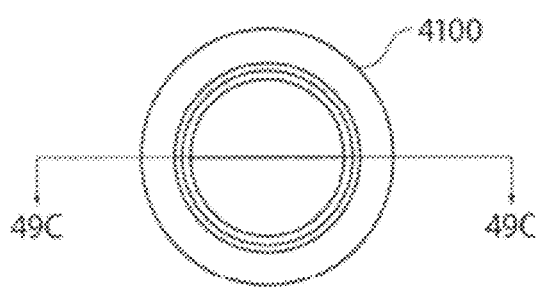
FIGS. 14A-14C show an exemplary eyelet that may be used to pivotably connect modular components of tissue closure devices.
Figure 14B:
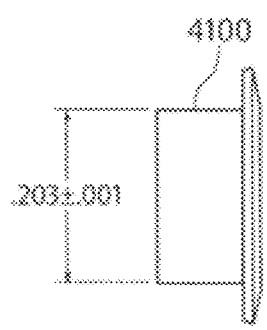
Figure 14C:
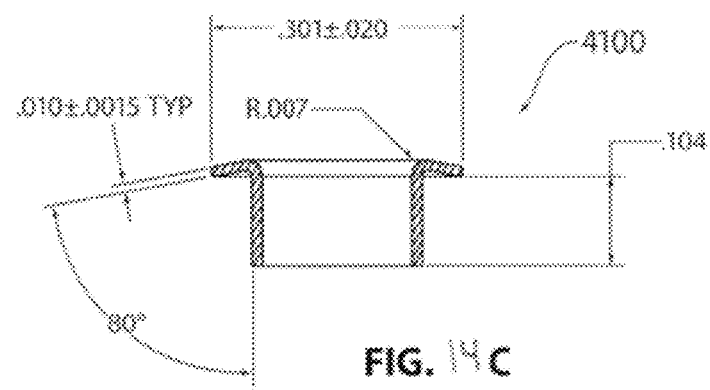

FIGS. 14A-14C show various views of an exemplary eyelet 4100 that may be used with any of the tissue closure devices described herein. During assembly of the various devices, orbital riveting may be used to achieve a minimal profile of eyelet 4100, so that it protrudes from the sternum or other tissue as little as possible. FIGS. 14A-14C show exemplary eyelet 4100 before a lower flare is formed by orbital riveting. In some embodiments, eyelet 4100 is formed from 6 gage 316 stainless steel tubing having a wall thickness of 0.010 inches, and is given a hard temper. Eyelet 4100 may have a nominal outer diameter of 0.203 inches, and an outer flare diameter of 0.301 inches.

In some embodiments of the modular devices described above, the bands are formed from 316L stainless steel, have a width of about 0.138 inches and a thickness of about 0.012 inches. In some embodiments, the overall length of bands 4000 and 4502 is about 10 to 14 inches and the overall length of bands 4500 is about 1.2 inches. In some embodiments, the enlarged mid-portions and end portions of the bands have an outer diameter of about 0.5 inches, with an aperture 4006 there-through having an inside diameter of 0.252 inches. In some embodiments, the center of buckle 4002 is placed about 0.860 inches from the center of aperture 4006.

FIG. 15A shows another embodiment of a tissue closure device. Device 5000 may be formed from a first band 5002 and a second band 5004. A buckle 4002 may be located at one end of each band 5002 and 5004. In this embodiment, band 5002 includes an offset mid-portion 5006, and band 5004 includes an offset mid-portion 5008. Each offset portion is provided with a circular aperture 4006. To fabricate device 5000, the offset portions 5006 and 5008 may be placed over one another such that the apertures 4006 align. An eyelet 4100, such as previously described, may then be inserted through apertures 4006 and secured in place by orbital riveting. This arrangement creates an H-shaped device 5000 as shown, with bands 5002 and 5004 pivotably coupled to one another at their mid-portions. Bands 5002 and 5004 are able to pivot relative to one another and/or eyelet 4100 about the common center point of apertures 4006 in this embodiment. In use, the distal end portion of each band may encircle tissue such as portions of a sternum and be received in the buckle 4002 located at the opposite end of the band.

FIG. 15B shows an alternative embodiment of device 5000. In this embodiment, the aperture 4006' in at least one of the offset portions 5006 and 5008 is elongated rather than circular. This allows eyelet 4100 to slide with respect to the elongated aperture 4006', thereby allowing the width W (shown in FIG. 15A) between bands 5002 and 5004' to be adjusted prior to or during installation.

FIG. 15C shows another alternative embodiment of device 5000. In this embodiment, buckles 4002 are located for installation on opposite sides of a sternum. This arrangement allows the closure device to be fabricated from two identical bands 5004, rather than from two symmetrically opposite bands 5002 and 5004 as shown in FIG. 15A.

FIG. 55 shows another feature that may be incorporated into any of the closure devices disclosed herein. Band 5500 is shown with at least a portion 5502 of its top surface having a texture applied. Such a surface may be created by knurling, dimpling, etching, or other well known processes. Surface portion 5502 may be provided with a coating having a high coefficient of friction. Such texturing and/or coating may be located on both the top and bottom surfaces of a band, and/or on multiple bands. Surface portion 5502 can provide a grip interface between mating bands and/or the underlying tissue to inhibit movement after the band(s) have been implanted.

FIG. 56 shows another exemplary tissue closure device 5600. Device 5600 may be formed by pivotably coupling two bands 5602 and 5604 at a mid-portion of each band, in a similar manner to the previously described modular devices. When assembled, device 5600 forms an H-shaped device similar to device 5000 shown in FIG. 15A.

FIGS. 16-18 show various alternatives for forming buckles and other locking mechanisms, and for securing bands of tissue closure devices with the locking mechanisms. Referring first to FIGS. 16A-16C, an exemplary method for forming buckle 3616 on strap 3614 will be described. FIG. 16A shows a plan view of the distal end of strap 3614 that has been punched out of sheet material with a T-shaped pattern for forming buckle 3616. Interlocking features 5800 and 5802 may be provided on opposing ends of the T-shaped pattern. The distal end of strap 3614 forms the bottom of buckle 3616. The pattern may be first bent along two bend lines 5804 to form two vertically extending side walls. The pattern may then be bent along two other bend lines 5806 such that the ends of the T-shaped pattern come together and form the top of buckle 3616. The interlocking features 5800 and 5802 engage each other as shown in FIG. 16B to keep buckle 3616 from coming apart when securing a band. In some embodiments, Interlocking features 5800 and 5802 may be welded together. In other embodiments, such as shown in FIG. 61A, the interlocking features may be omitted. Depending on the loading configuration of the buckle, the straight butt joint may be welded or left unwelded. Buckle 3616 may be configured to receive one, two, or more bands there-through.

Figure 17A:
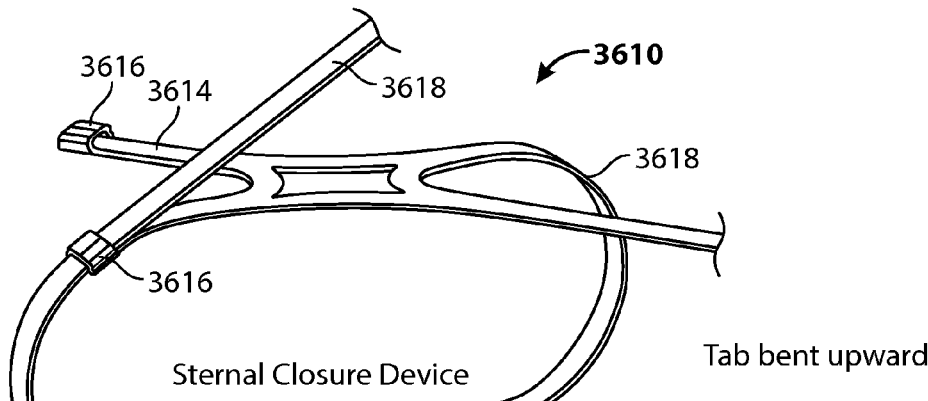
FIGS. 17A-17D show details of locking an exemplary band relative to a buckle.
Figure 17B:
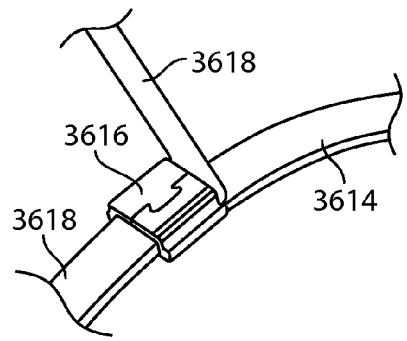
Figure 17C:
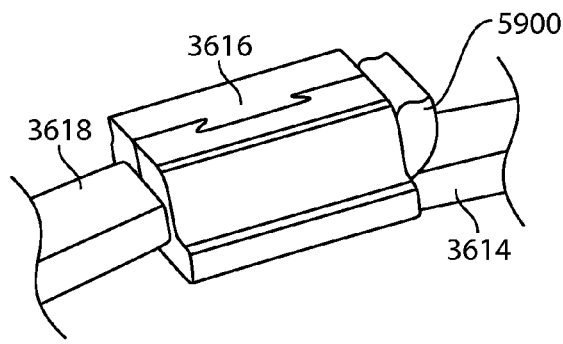
Figure 17D:
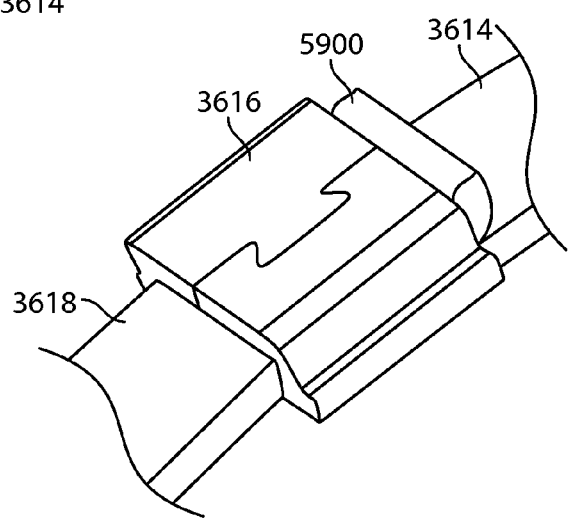

FIGS. 17A-17D show one embodiment for securing band 3618 in buckle 3616. FIG. 17A shows one of the bands 3618 of device 3610 inserted into one of the buckles 3616. During installation on a sternum or other tissue, a surgeon may temporarily secure a band 3618 in place by bending the band upward, as shown in FIG. 16B. The surgeon may then straighten the band, readjust it, and secure it again by re-bending the band 3818. A tensioning tool, as previous described, may be used to place a variable or predetermined tension on band 3618 relative to buckle 3616 and place a bend in band 3618 to secure it. The same tool, or a different tool, may be used to shear off excess band 3618. The cutting tool may shear band 3618 in a predetermined location, such as adjacent to the top of buckle 3616, as shown in FIGS. 17C and 17D. In this manner, an L-shaped end 5900 is left on the distal end of tensioned band 3618 to prevent the distal end of band 3618 from being pulled back through buckle 3616.

Figure 18A:
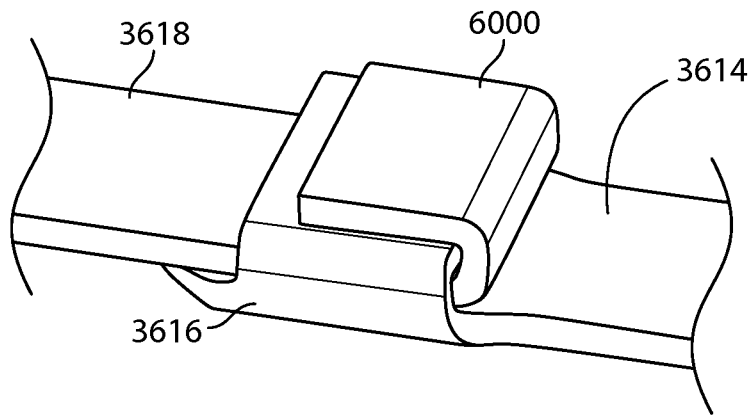
FIGS. 18A-18B show details of locking an exemplary band relative to a buckle.
Figure 18B:
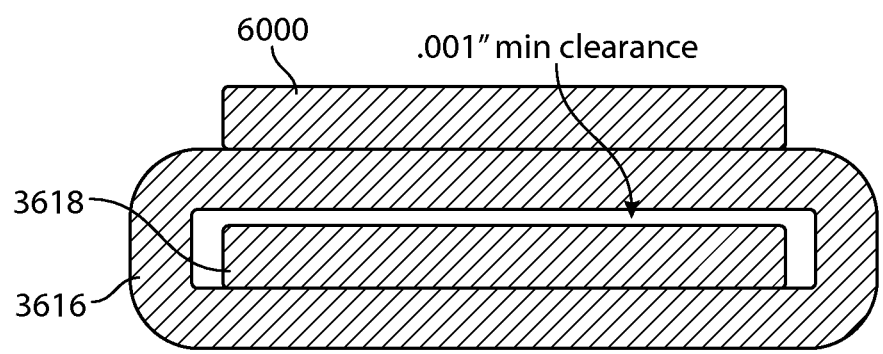

FIGS. 18A-18B show another embodiment for securing band 3618 in buckle 3616. As shown, the distal end of band 3618 may be formed into a U-shaped portion 6000 that wraps around the top of buckle 3616. Such an arrangement can help an unwelded buckle 3616 remain intact under load. This securing method may be accomplished manually, or specialized tensioning, bending and cutting tool(s) can be configured to perform these operations more quickly and consistently, as described below.

FIGS. 19A-19C show further details of one particular sternum band configuration. A buckle 4002 and a short section of band 4500 are pivotably attached with a rivet 4100 to a long section of band 4502 near the proximal end of the tissue closure device 4504, as previously described. A curved needle 6700 is welded to the distal end of device 4504 for threading the distal end of the band through tissue between the ribs and around the sternum. The needle 6700 is then cut off, and the distal end of band 4502 is inserted through buckle 4002. The band may then be tensioned and secured, as will next be described, and the excess band is then cut off.

Figure 24:
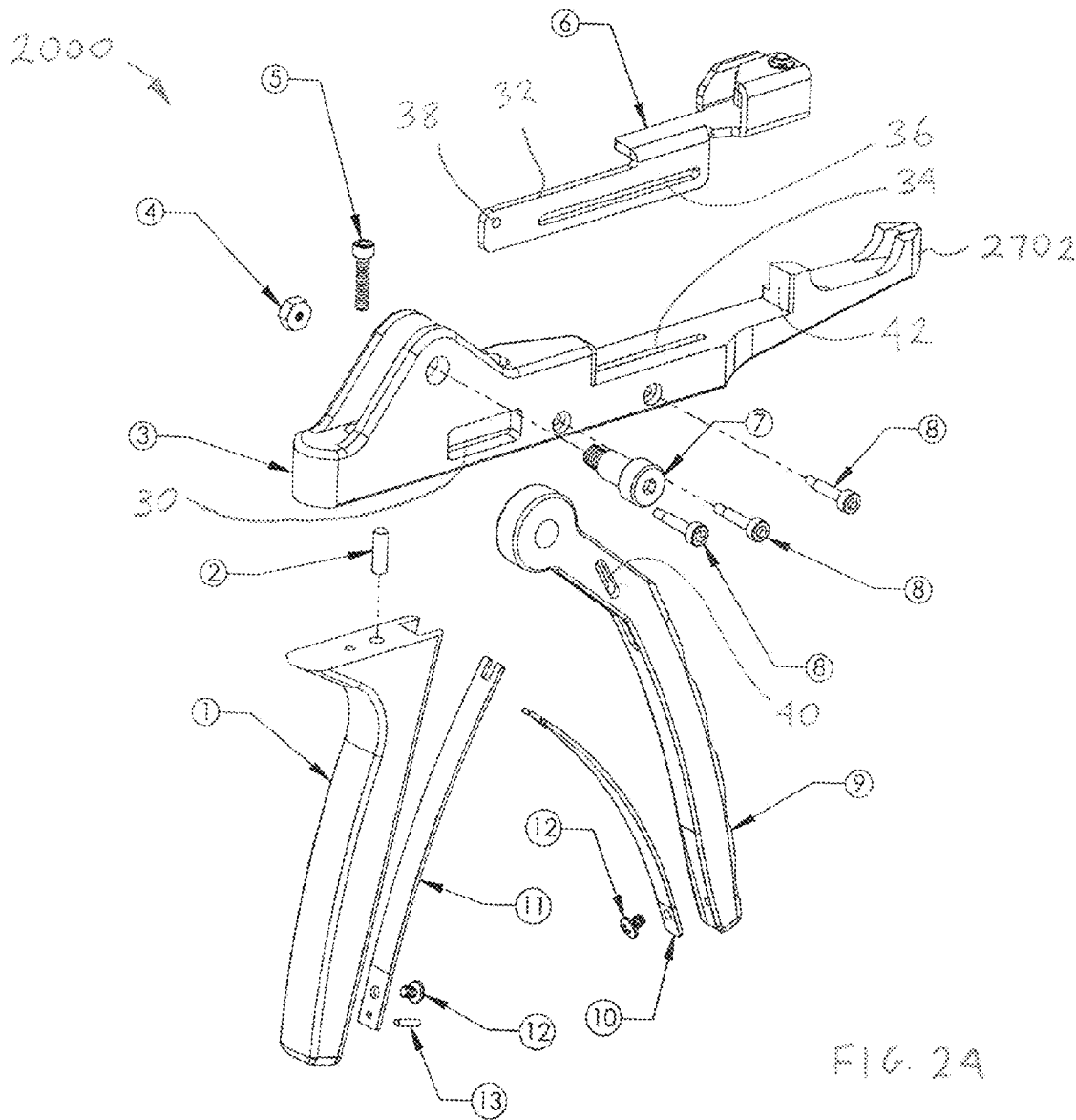

FIGS. 20-24 are various views showing an exemplary embodiment of a band tensioning device 2000 constructed according to aspects of the disclosure. Tensioning device 2000 may generally be used with any of the tissue closure bands disclosed herein. The main components of device 2000 include a handle 1, a main body 3, a carrier 6, a trigger 9, a trigger leaf spring 10, and a handle leaf spring 11. Handle 1 depends from the lower proximal end of main body 3, and as best seen in the exploded view of FIG. 24, is secured to main body 3 with pin 2 and screw 5. The proximal region of main body 3 includes an internal cavity that is partially open to the exterior at the upper and lower surfaces of main body 3. The internal cavity is also partially open to the exterior through a window 30 on each side of main body 3. The upper end of trigger 9 is received through the bottom of main body 3 and into the internal cavity. The upper end of trigger 9 is pivotably mounted within main body 3 by a shoulder screw 7, which passes through a hole in an upper flange of main body 3, through a hole in the upper end of trigger 9, and is then threaded into a hole in another upper flange on the opposite side of main body 3. A lower end of a cantilevered leaf spring 10 is secured to trigger 9 by a screw 12. A lower end of an opposing cantilevered leaf spring 11 is secured to handle 1 by a pin 13 and screw 12. The upper ends of leaf springs 10 and 11 may be provided with an inter-engaging tongue and groove arrangement, as best seen in FIG. 24, so that the upper ends of the springs can pivotably engage each other, as best seen in FIG. 20. With the above-described arrangement, handle 1 and trigger 9 can be grasped when in the open position shown in FIG. 20, and trigger 9 may then be pivoted in a proximal direction towards a closed position with handle 1, as shown in FIG. 21. Leaf springs 10 and 11 provide a return force that urges trigger 9 back to the open position of FIG. 20. In some embodiments, leaf springs 10 and 11 are easily removable to facilitate sterilization and reuse of device 2000. In other embodiments, device 2000 is configured to be disposable after being used in a single procedure.

Referring again to FIG. 24, tensioner device 2000 includes a carrier subassembly 6 that in operation slides along the top surface of main body 3. Carrier 6 has a downwardly projecting fin 32 that serves to slidably retain carrier 6 on main body 3. Fin 32 is slidably received within a longitudinally oriented slot 34 through the top of main body 3. Fin 32 includes a longitudinal slot 36. A pair of shoulder screws 8, 8 pass through holes in one side of main body 3, through slot 36 in fin 32, and thread into holes in the opposite side of main body 3. This arrangement captivates carrier 6 on main body 3, but allows it to slide along a proximal/distal path.

Fin 32 of carrier 6 also includes a through-hole 38 near its proximal end for attaching to trigger 9. A slot 40 is also provided near the upper end of trigger 9 for attaching to fin 32. When attaching carrier 6 to trigger 9, a shoulder screw 8 is passed through window 30 on one side of main body 3, through hole 38 in fin 32, through slot 40 in trigger 9, and threaded into a locknut 4 located in window 30 on the opposite side of main body 3. With this arrangement, when trigger 9 is pivoted rearward/proximally toward handle 1, shoulder screw 8 and locknut 4 move upward relative to slot 40 in trigger 40, but directly rearward in windows 30, 30 relative to main body 3. The rearward movement of shoulder screw 80 draws fin 32 rearward, causing carrier subassembly 6 to slide rearward along the top of main body 3, as shown in FIG. 21. When trigger 9 is released, leaf springs 10 and 11 urge trigger 9 in a forward/distal direction, causing carrier subassembly 6 to return to a forward position, as shown in FIG. 20. When carrier subassembly 6 is moved to the forward position, it abuts a carrier stop member 42 that projects upwardly from main body 3, as will be subsequently described in further detail.

Figure 25:
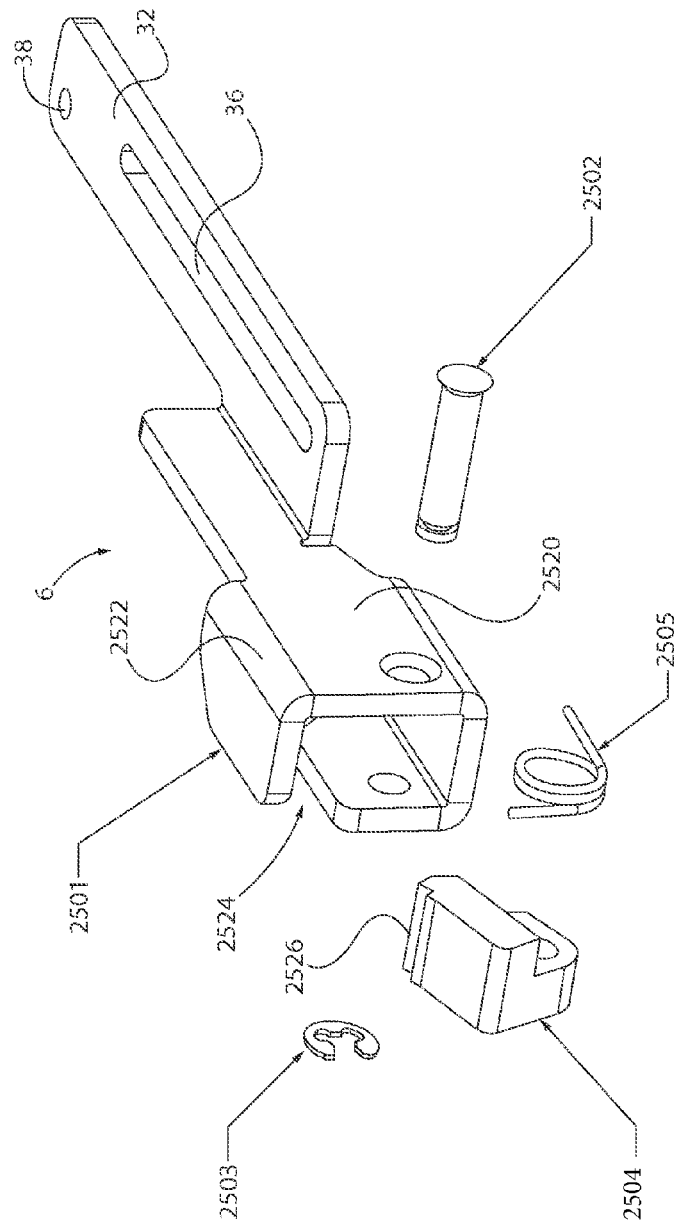
FIG. 25 shows an exploded view of the carrier subassembly of the tensioning device shown in FIGS. 20-24.

Referring to FIG. 25, the components of carrier subassembly 6 are shown in an exploded configuration. In this exemplary embodiment, carrier subassembly 6 includes a carrier 2501, a dog pin 2502, an external retaining ring 2503, a dog 2504 and a torsion spring 2505. Carrier 2501 has a bottom surface 2520 configured to slide along a top surface of the main body 3 of tensioner device 2000, as previously described. Carrier 2501 may be fabricated from sheet metal as shown, such that it forms a partially enclosed box section 2522. Box section 2522 includes a slot 2524 for receiving the distal end of a sternum band, as will be subsequently described in more detail.

Box section 2522 has holes through its top and bottom surfaces for receiving dog pin 2502. The hole in the bottom of box section 2522 may be chamfered as shown to receive the beveled head of pin 2502 in a countersunk configuration so that pin 2502 does not interfere with the sliding motion of carrier 2501. The interior of box section 2522 is configured to receive dog 2504. Dog 2504 is pivotably retained in box section 2522 by pin 2502, which passes through a hole in a portion of dog 2504. Pin 2502 is held in place by retaining ring 2503, which snaps over the end of pin 2502 as it protrudes through the top surface of box section 2522. Torsion spring 2505 resides within box section 2522, around pin 2502 and within a cutout portion of dog 2504. One leg of torsion spring 2505 presses against an inside wall of box section 2522 while the other leg presses against an opposing wall of the cutout portion of dog 2504. With this arrangement, torsion spring 2505 resiliently urges a toothed end portion 2526 of dog 2504 against an opposite inside wall of box section 2522 adjacent to slot 2524.

Referring to FIGS. 26A and 26B, the operation of dog 2504 and carrier subassembly 6 will now be described. FIG. 26B shows carrier subassembly 6 pulled proximally away from carrier stop 42 in the direction of Arrow B. In this position, torsion spring 2505 urges toothed end portion 2526 of dog 2504 against the opposing vertical wall of box section 2522, as previously described in relation to FIG. 25. As also previously described, the forward/distal position of carrier subassembly 6 on main body 3 shown in FIG. 26A is the default position when trigger 9 is released and springs 10 and 11 urge carrier subassembly 6 forward. When carrier subassembly 6 moves from the more proximal/rearward position of FIG. 26B toward the forward/distal position shown in FIG. 26A, a forwardly protruding portion of dog 2504 contacts carrier stop 42. Further movement of carrier subassembly 6 in the direction of Arrow A towards the forward position causes dog 2504 to be rotated counter-clockwise by carrier stop 42 against the force of torsion spring 2505 (shown in FIG. 25). This motion opens up a gap between the toothed end portion 2526 of dog 2504 and the opposing vertical wall of box section 2522, making it easier to engage a distal end of a sternum band in slot 2524, in a top-loading manner, as will be subsequently described in more detail. A laterally ramped surface 2602 may be provided on main body 3 distal to carrier stop 42, as shown, to aid in engaging a band in slot 2524.

Once a band is top-loaded into slot 2524 of carrier subassembly 6 and trigger 9 (shown in FIG. 20) is squeezed, carrier subassembly 6 moves proximally in the direction of Arrow B. This movement disengages dog 2504 from carrier stop 42 and allows torsion spring 2505 (shown in FIG. 25) to rotate teeth 2526 of dog 2504 into engagement with the band. Further squeezing of trigger 9 causes carrier subassembly 6 to draw the band in the proximal direction of Arrow B.

Figure 27:
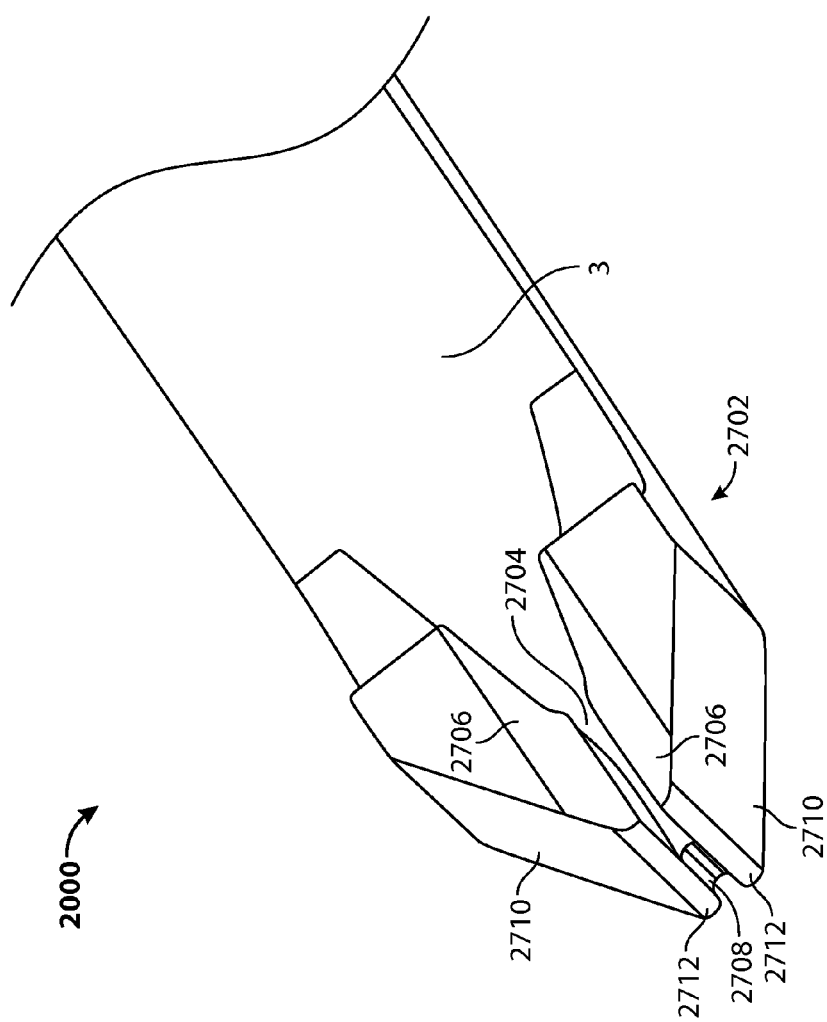
FIG. 27 shows the distal tip portion of the device shown in FIGS. 20-24.

Referring to FIG. 27, the distal tip 2702 of tensioner device 2000 is shown. Slot 2704 is centrally provided through tip 2702 for receiving and stabilizing a band to be tensioned. Chamfered lead-in surfaces 2706 are provided on the distal tip 2702 as shown to aid in engaging slot 2704 with the band. A notch 2708 may also be provided at the distal end of the bottom of slot 2704 to aid with band engagement.

According to aspects of the invention, distal tip 2702 of this embodiment is also provided with angled faces 2710. Angled faces 2710 allow tip 2702 to reach deep into a chest cavity, from either the left or the right side of the patient, to engage with a band buckle, as will be subsequently described in more detail. Angled faces 2710 also provide the surgeon with increased visibility of the sternum band and surrounding anatomy during band tensioning. In some embodiments, angled faces 2710 are symmetrically formed with respect to the central longitudinal axis of device 2000, and form an included angle of about 75 degrees. In other embodiments, the included angle is less than 75 degrees. The distal edges 2712 of angled faces 2710 may have a rounded profile as shown for better engagement with the band buckle.

Figure 28A:
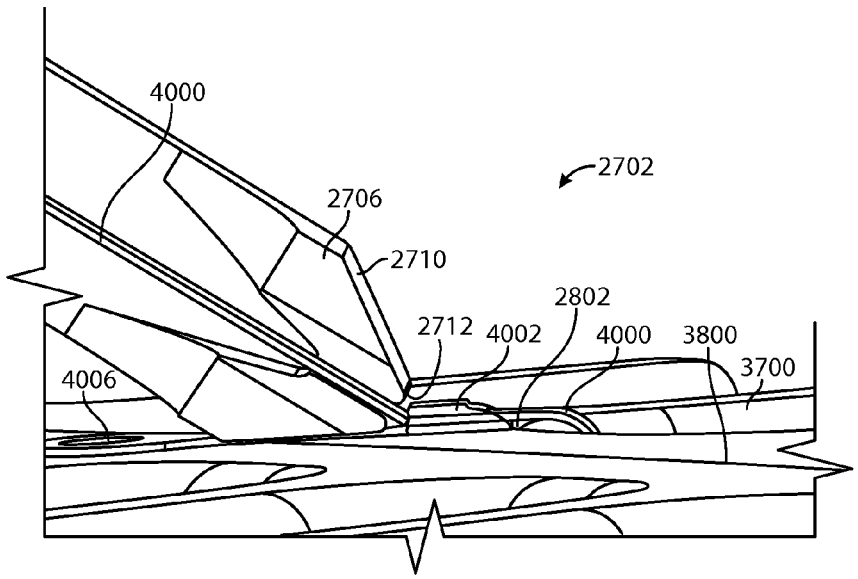
FIGS. 28A and 28B show the distal tip portion of FIG. 27 engaged with a portion of a closure device on a sternum.
Figure 28B:
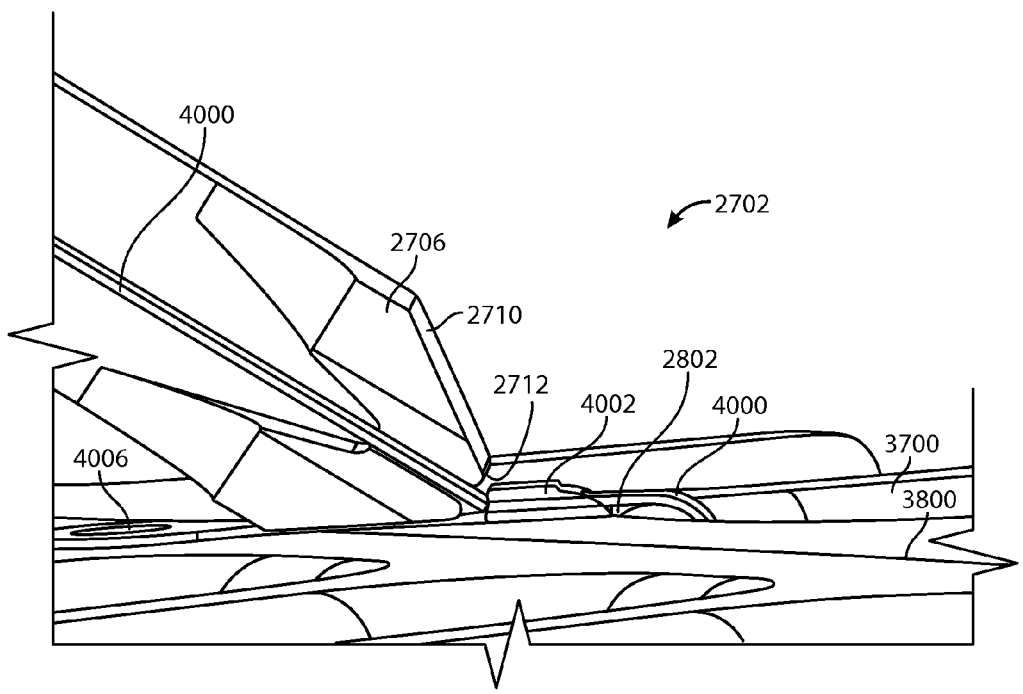
Figure 29:
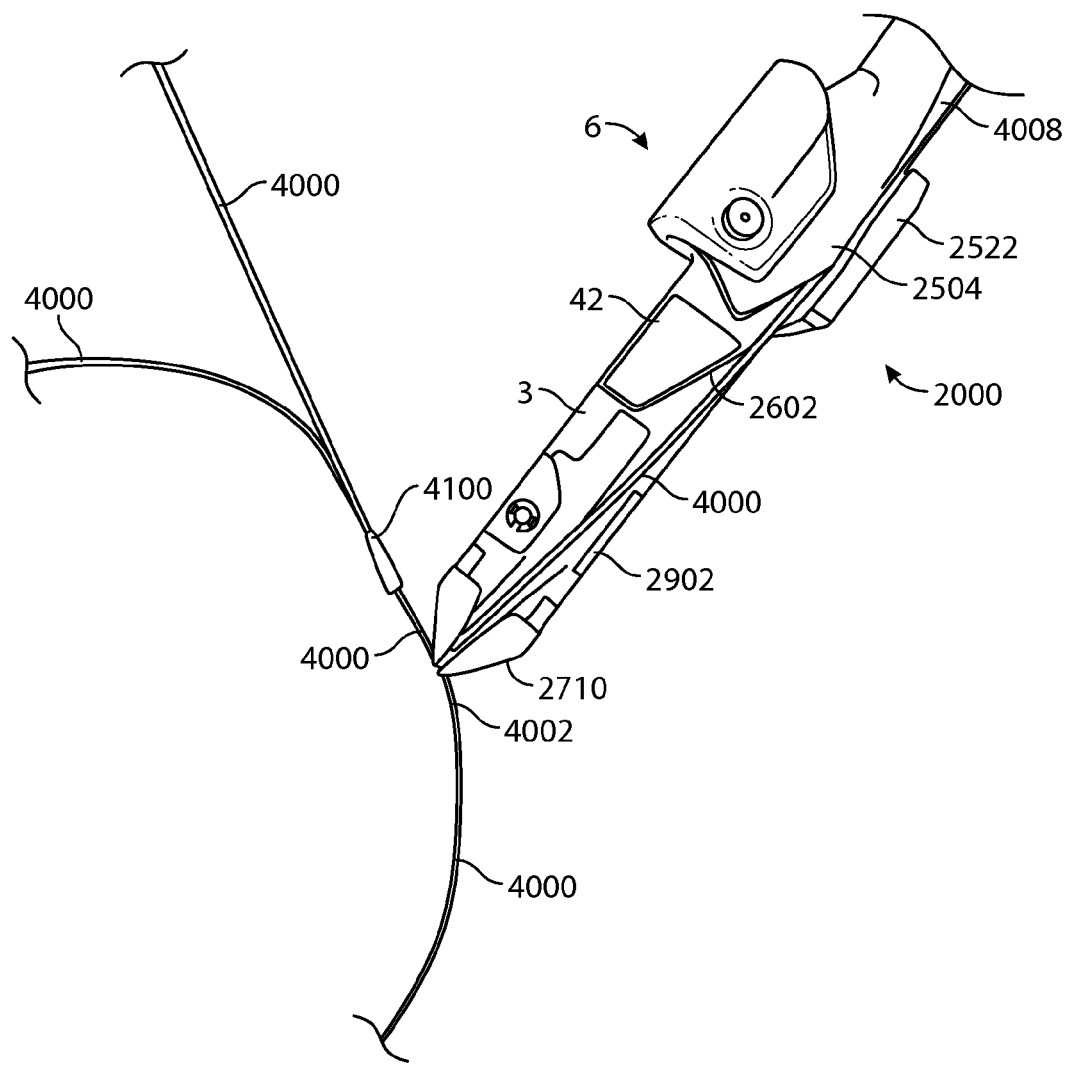
FIG. 29 shows a portion of a tensioning device engaged with a closure device.

Referring to FIGS. 28A, 28B and 29, tensioner device 2000 is shown engaged with sternum band 4102. As previously described with reference to FIG. 6, sternum band 4102 includes two bands 4000 pivotably coupled together with rivet 4100. However, only a single band 4000 is shown in FIGS. 28A and 28B for clarity. As best seen in FIG. 28A, one of the angled faces 2710 of the distal tip 2702 of device 2000 is in contact with sternum band 4000 between buckle 4002 and rivet aperture 4006. The distal end 4008 of one of the two bands 4000, after passing around sternum 3700 and through band buckle 4002, is received through slot 2704 in the distal tip 2702 of device 2000. As shown in FIG. 29, band 4008 spans an open portion 2902 of main body 3 between slot 2704 and carrier stop member 42, and is captured by dog 2504 of carrier subassembly 6 for tensioning. Open portion 2902 allows enhanced visibility of the surgical site, buckle 4002 and bands 4000 and 4008. In some embodiments, the distance D of open portion 2902 (as shown in FIG. 23A) is about 1.0 inch. In other embodiments, the open portion between a raised distal tip of the device and a raised carrier stop member is between about 1.0 and about 4.0 inches.

Referring to FIGS. 30A, 30B and 31, several exemplary embodiments of sternum bands are depicted in their final tensioned positions around sternum 3700, closing cut line 3800 in the sternum. FIG. 30A shows a single band 4000, FIG. 30B shows an figure 8 or X-shape device 4102, and FIG. 31 shows an H-shape device 5000, the construction and operation of which have all been previously described. To close a sternum 3700 after a sternotomy, one or more of these devices may be positioned around the sternum. As previously described, a curved needle 6700 (shown in FIG. 19A) located on the distal end 4008 of each band 4000 is pushed through the tissue between two ribs and around the posterior side of sternum 3700. The needle(s) are then cut off, such as by using surgical scissors. The distal end 4008 of each band 4000 is then threaded through its associated buckle 4002. It is noted here that several features may be employed on the sternum bands to aid threading the distal ends 4008 through buckles 4002. First, a tongue 2802 (shown in FIGS. 28A and 28B, and also seen in earlier figures such as FIGS. 16A-C) may be provided at the distal end of buckles 4002. Second, the width of the distal ends 4008 of bands 4000 may be made narrower than the width of the proximal ends, as shown in FIG. 19A. This allows some play between the band and the buckle slot when first being engaged, to permit some angular misalignment between the two. Once the band is pulled through the buckle and pulled snug, the wider proximal portion of band 4000 can provide a friction fit inside buckle 4002 to help hold the band in place before it is tensioned with tensioner 2000. In some embodiments, the distal end 4008 of each band 4000 is at least 0.010 inches narrower than the proximal end. In some embodiments, the distal end 4008 of each band 4000 is at least 0.020 inches narrower than the proximal end.

Once the sternum closure device(s) are loosely in place around the sternum 3700, they may be manually pre-tensioned before using tensioner 2000, if desired. In some embodiments, the sternum closure device is configured so that eyelet aperture 4006 is easily aligned with sternum cut 3800 along the centerline of sternum 3700. This places buckle(s) 4002 just off the anterior surface of sternum 3700, as shown in FIGS. 30A, 30B and 31, so that buckle(s) 4002 are still readily accessible to the surgeon but do not protrude from the patient's chest after the procedure is completed. Each band 4000 may be sequentially tightened and retightened by bending the loose end of the band downward, pulling the band laterally relative to the buckle 4002, and then pulling the band 4000 generally upward, such as at an angle of 45 to 90 degrees to the buckle, to temporarily secure band in place. Each band 4000 can be tightened and or loosened any number of times until the surgeon is satisfied with the position of the portions of the cut sternum and the closure device(s).

Either after or instead of pretensioning the closure device(s) as described above, tensioner 2000 may be attached to the loose end of a band 4000 emerging from buckle 4002. The distal tip 2702 of device 2000 may be applied to band 4000 such that band 4000 engages with slot 2704. Band 4000 may then be placed in slot 2524 of carrier subassembly 6, as shown in FIG. 29. When the trigger of device 2000 is squeezed, the distal tip 2702 of device 2000 advances along band 4000 until it buts up against buckle 4002. Further squeezing of the trigger causes band 4000 to be tensioned against the buckle. When the desired tension is achieved, tensioning device 2000 may be tilted upward to bend band 4000 to a generally right angle relative to buckle 4002. Tensioner 2000 may then be removed from band 4000. Once all of the bands have been tensioned, and retensioned if desired, their ends may be cut off with surgical scissors and folded over the top of buckles 4002 to permanently secure them in place, as shown in FIGS. 30A, 30B and 31.

The same tensioner 2000 may be used by a right-handed or left-handed surgeon. A right-handed surgeon will typically stand on the right side of the patient, who is in a supine position, such that the patient's head is to the surgeon's left when he or she faces the patient. The curved needle(s) of the closure device(s) are typically inserted between the ribs on the near side of the sternum, and emerge from the far side of the sternum. This places the buckle(s) on the opposite side of the sternum from the surgeon. Top-loading tensioner device 2000 is then applied to the caudal side of the band(s), with the handle of the device pointing toward the patient's feet. This arrangement provides better visibility and a more comfortable hand position for the surgeon. If the tensioner device were to be side-loading, its handle would be pointing toward the surgeon, making it less comfortable to operate and potentially blocking the surgeon's view of the sternum and closure device(s). A left-handed surgeon will typically stand next to the opposite side of the operating table, to the patient's left. The procedure is the same as for a right-handed surgeon, and the handle of the tensioning device 2000 again points toward the patient's feet.

In some embodiments, the handle of device 2000 may be configured at an angle relative to its main body 3. An angle of up to 45 degrees in either direction provides the surgeon with a comfortable operating position. In other words, instead of a surgeon's hand being generally parallel with a sagittal plane of a patient when using the device, as with the embodiment shown in the figures, in these other embodiments the surgeon's hand may form an angle in the range of plus or minus 45 degrees relative to the sagittal plane.

During a sternum closure procedure, a surgeon's hand typically moves in a medio-lateral direction plus and minus about 45 degrees from vertical. As can be appreciated from FIGS. 30A, 30B and 31 and the preceding descriptions, buckle(s) 4002 of the closure devices typically are oriented about 45 degrees from horizontal when in their final positions. Accordingly, tensioner device 2000 typically tips about 45 degrees toward the surgeon initially when it is being engaged with a band 4000. Tipping device 2000 towards vertical will then apply about a 45 degree bend to band 4000. Tipping device 2000 further, about 45 degrees away from the surgeon, applies about a 90 degree bend to band 4000.

Referring to FIGS. 32A and 32B, another sternum closure device 3200 constructed according to aspects of the invention is shown. Device 3200 is similar to the device shown in FIG. 30A, but includes two apertures 3202. In this exemplary embodiment, closure device 3200 is formed from a single band and does not pivot. However, in other embodiments, band pivots as previously described may be incorporated. The apertures 3202 are spaced such that they reside on the anterior face of sternum 3700 on opposite sides of cut line 3800. Each aperture 3202 may be surrounded with an enlarged band portion as shown to increase the surface area contacting the anterior surface of sternum 3700. In other embodiments, the entire anterior surface of the closure device is enlarged relative to the band that encircles the posterior of the sternum.

Apertures 3202 are configured to each receive a bone screw 3204 after band tensioning. As shown in FIG. 32B, when bone screws 3204 are tightening down on sternum 3700, device 3200 is further secured on both sides of sternum cut line 3800. This arrangement allows device 3200 to provide additional fixation to the cut portions of the sternum. Namely, device 3200 can further resist relative movement of the sternum portions in the anterior/posterior direction and in the cranial/caudal direction.

Figure 33:
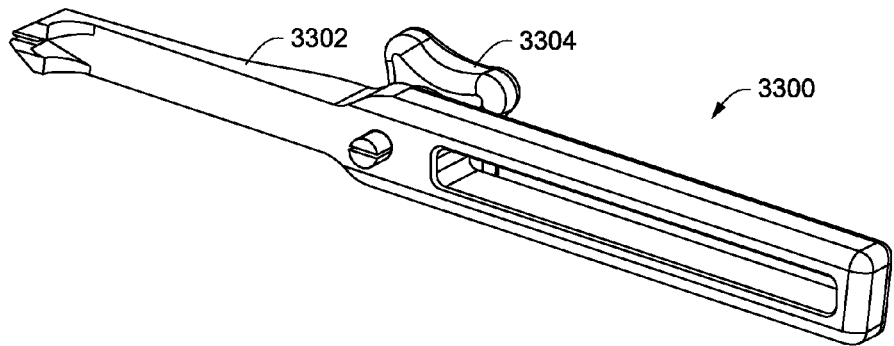
FIGS. 33-45B show various views of alternative band tensioning devices.
Figure 34:
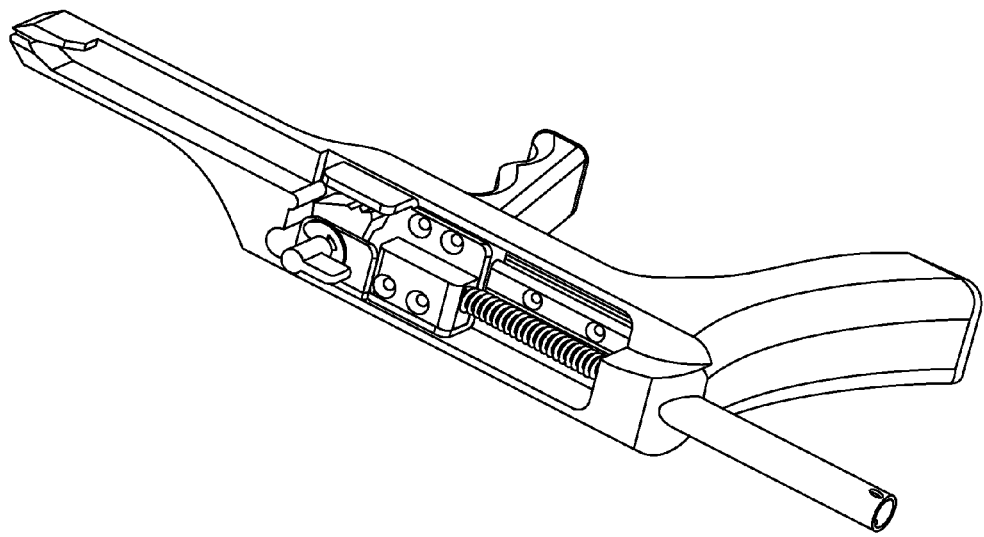
Figure 35A:
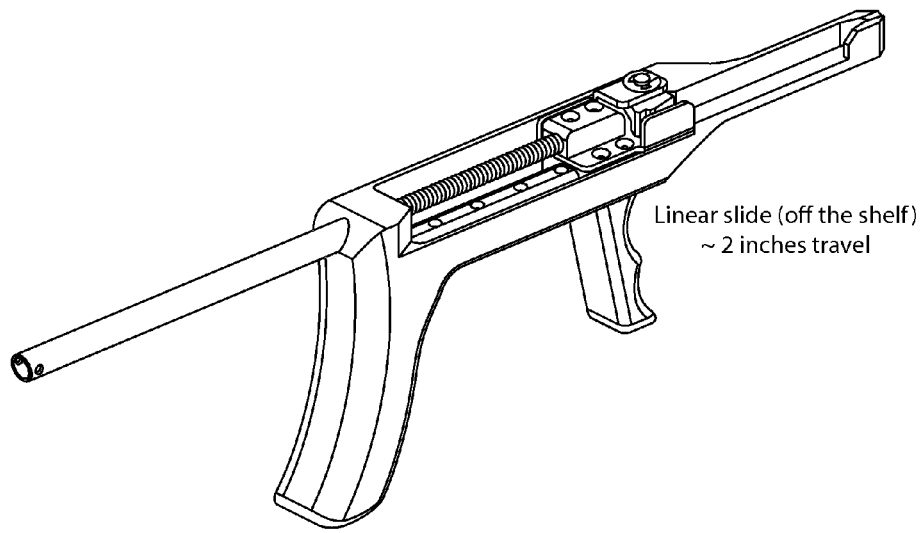
Figure 35B:
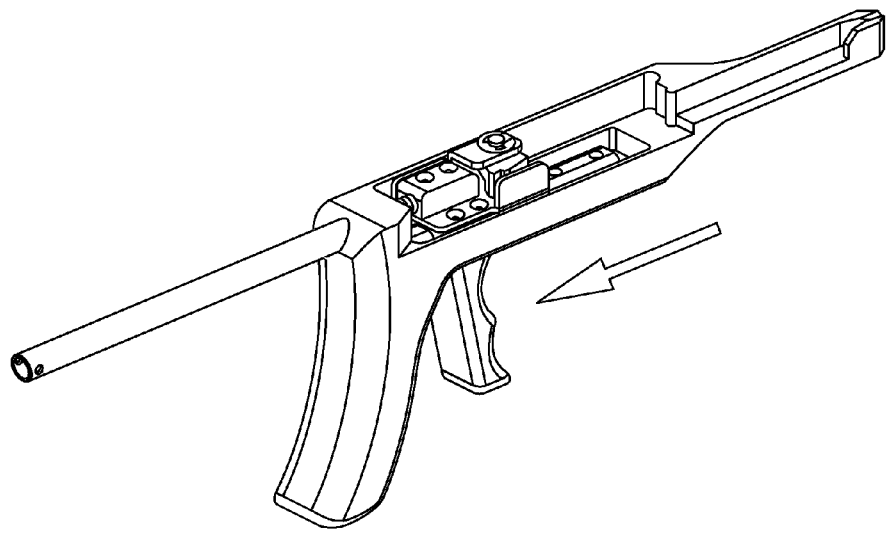

Referring to FIG. 33, another tensioning device embodiment is shown. Device 3300 includes a slotted pin 3302 for receiving the distal end of a sternum band. Knob 3304 is provided to rotate pin 3302, thereby winding the band around pin 3302 to increase its tension.

Referring to FIGS. 34-45B, additional tensioning device embodiments are shown.

Referring to FIGS. 46A-46C, an alternative band tensioning device 4600 is shown. As shown in FIG. 46A, band tensioning device 4600 is similar in design and operation to previously described device 2000. As best seen in FIGS. 46B and 46C, device 4600 includes an actuation lever 4602 located on dog 4604. In this particular embodiment, actuation lever 4602 is integrally formed with dog 4604 and extends proximally towards the handle of device 4600. Actuation lever 4602 includes a thumb grip 4606 which may be knurled or have ridges for better gripping by a surgeon's thumb, finger or palm. In this embodiment, thumb grip 4606 forms an angle of about 45 degrees with the main portion of actuation lever 4602. Both the thumb grip 4606 and the main portion of actuation lever 4602 lie within the lateral boundaries of device 4600 to inhibit accidental actuation.

In operation, actuation lever 4602 allows a surgeon to release dog 4604 from contact with opposing inside wall 4608 of the box section, or from contact with a band (not shown in these figures for clarity). This may be useful to open a gap between dog 4604 and wall 4608 when first inserting a band, or to release the band once it has been tensioned and bent to hold the band in place. FIG. 46B shows dog 4604 in a closed position, biased by a spring as previously described in reference to device 2000. FIG. 46C shows dog 4604 in an open position, after actuation lever 4602 has been rotated in the direction of Arrow A. When band tensioning device 4600 is held in the right hand of a surgeon, the surgeon may use his or her right thumb or a portion of the left hand to operate actuation lever 4602.

Referring to FIGS. 47A-47E, a series of steps depicting another exemplary method of securing a band is shown. As previously described, a band 4700 having a buckle 4702 at its proximal end and a curved needle (not shown) at its distal end is passed around two portions of a sternum. The needle is then cut off, and the distal end of band 4700 is inserted through buckle 4702 and snugged up by hand. After the desired tension is placed on band 4700 using a tensioning device, such as device 2000 or 4600 as previously described, the distal end of band 4702 is bent upwardly with device 2000 at about a 90 degree angle relative to the proximal end of band 4700, as shown in FIG. 47A. Multiple straps are typically used to close a sternum, with each strap being progressively tightened in sequence, moving from the cephalad end toward the xiphoid. At the start of the securing procedure depicted by FIGS. 47A-47E, the distal tip 2702 of device 2000 is placed on the distal end of band 4700 adjacent to where it emerges from buckle 4702 such that band 4700 resides in slot 2704 of device 2000. At this point, the distal end of band 4700 typically is not engaged in dog 2504 (not shown) and there is no tension being placed on the distal end of band 4700.

As shown in FIG. 47B, once the distal tip 2702 of device 2000 is engaged with the distal end of band 4700, device 2000 is rotated about a central longitudinal axis 4704 (shown in FIG. 47C) of the distal end of band 4700. Axis 4704 is also generally along the longitudinal axis of device 2000. In this exemplary embodiment, the distal end of band 4700 is rotated about 120 degrees in a clockwise direction, as shown by Arrow A. In other words, the tip 2702 of device 2000 stays generally in place while the handle (not shown) of device 2000 is rotated about the longitudinal axis of device 2000 about 120 degrees. In a typical procedure, the handle of device 2000 is first pointing in the caudal direction of the patient, is rotated toward the surgeon who is standing on the right side of the patient, and then ends up pointing toward the left side of the surgeon.

FIG. 47C shows the distal end of band 4700 after it has been rotated about 120 degrees around central longitudinal axis 4704. In this step, the distal end of band 4700 is cut so that it remains about 0.7 to 1.0 cm long as shown.

In the step depicted by FIG. 47C, the cut distal end of band 4700 is folded to one side, generally in half, and back onto itself 180 degrees.

In the step depicted by FIG. 47E, the folded distal end of band 4700 is bent down over and to one side of the proximal end of band 4700. In this configuration, the sternum band construct lays flat on top of or laterally to one side of the sternum with a low profile that does not protrude outwardly any significant amount. Tension is securely maintained on band 4700 by the twist and fold in the distal end of band 4700.

In some embodiments of the above exemplary method, the distal tip 2702 of device 2000 is facing the opposite direction shown in FIG. 47A when placed on band 4700, such that the back/bottom side of distal tip 2702 would be seen in FIG. 47A and the front/top side of distal tip 2702 would be seen in FIG. 47B. In some embodiments, the cut distal end of band 4700 is folded back on itself in the opposite direction from that shown in FIG. 47D. In some embodiments, the folded distal end of band 4700 is bent down over the proximal end of band 4700 such that it extends off the opposite side of the proximal end from that shown in FIG. 47E.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. Features of disclosed embodiments may be used in combination with features of other embodiments. It is therefore contemplated that the invention shall also cover any such modifications, variations and equivalents.

What is claimed as the invention is:

1. A band tensioning device comprising:
   a main body having proximal and distal ends, a top side and a bottom side, the top side being spaced from the bottom side in a vertical direction;
   a handle depending downwardly from the bottom side of the main body at the proximal end of the main body and immovably affixed thereto;
   a trigger depending downwardly from the bottom side of the main body at the proximal end of the main body distal to the handle and movably affixed to the main body;
   a carrier movably coupled to the main body such that it moves proximally and distally in a longitudinal direction along the main body, the carrier being linked to the trigger such that when the trigger is moved proximally toward the handle, the carrier is pulled proximally along the main body by the trigger, the carrier having a vertically extending surface accessible by a smooth band inserted from the top side of the main body;
   a dog pivotably mounted to the carrier, the dog having a toothed engagement surface configured to pinch the band between itself and the vertically extending surface of the carrier; the dog configured to pivot between a closed position against the band or the vertically extending surface and an open position away from the vertically extending surface; and
   a spring spanning between the carrier and the dog to bias the dog towards the closed position,
   wherein the distal end of the main body includes a vertically extending slot accessible by the band inserted from the top side of the main body such that a distal end of the band may be placed into the slot and between the dog and vertically extending surface of the carrier from the top side of the main body to tension the band.

2. The band tensioning device of claim 1, wherein the distal end of the main body comprises vertically oriented angled surfaces symmetrically formed with respect to a central longitudinal axis of device.

3. The band tensioning device of claim 2, wherein the angled surfaces form an included angle of about 75 degrees.

4. The band tensioning device of claim 2, wherein the angled surfaces form an included angle of less than 75 degrees.

5. The band tensioning device of claim 2, wherein the angled surfaces comprise distal edges having a rounded profile to provide better engagement with a band buckle.

6. The band tensioning device of claim 1, wherein the dog comprises a distally protruding portion configured to contact a carrier stop located on the main body to pivot the dog towards the open position.

7. The band tensioning device of claim 6, further comprising a laterally ramped surface at the top side of the main body distal to the carrier stop.

8. The band tensioning device of claim 1, wherein the dog comprises an actuation lever configured to allow manual actuation of the dog towards the open position.

9. The band tensioning device of claim 8, wherein the actuation lever extends from the dog proximally toward the handle, and further comprising a grip at a proximal end of the actuation lever.

10. The band tensioning device of claim 9, wherein the grip is angled relative to the actuation lever.

11. The band tensioning device of claim 10, wherein:
    the grip extends from the actuation lever at an angle of about 45°;
    the grip is knurled or has ridges to assist gripping by a user's thumb, finger, or palm; and
    in a default position, both the grip and the actuation lever lie within a boundary defined by lateral sides of the device to inhibit accidental actuation.

12. The band tensioning device of claim 1, wherein the device comprises a single dog.

13. The band tensioning device of claim 1, wherein the device cannot cut the band placed therein.

14. The band tensioning device of claim 1, wherein the main body is configured to generally expose the band spanning between the vertically extending slot and the vertically extending surface of the carrier for better visibility of the band by a surgeon.

15. The band tensioning device of claim 1, wherein an axis of rotation of the trigger is in a lateral direction different than the vertical direction.

16. The band tensioning device of claim 15, wherein an axis of rotation of the dog is in the vertical direction and is orthogonal to the lateral direction and the longitudinal direction.

17. The band tensioning device of claim 1, wherein the carrier comprises a downwardly projecting fin that is slidably received in a slot at the top side of the main body.

18. The band tensioning device of claim 17, further comprising a pair of screws passing through holes in a first lateral side of the main body, passing through a longitudinal slot in the fin, and threaded into holes in a second lateral side of the main body.

19. The band tensioning device of claim 17, wherein the fin is connected to the trigger by a screw passing through a through-hole in the fin and a slot in the trigger.

20. A band tensioning device comprising:
    a main body having a proximal end, a distal end, a top side, a bottom side, a first side, and a second side, wherein the top side is spaced from the bottom side in a vertical direction, and the first side is spaced apart from the second side in a lateral direction;
    a handle depending from the bottom side of the main body at the proximal end of the main body and immovably affixed thereto;
    a trigger depending from the bottom side of the main body at the proximal end of the main body distal to the handle, wherein the trigger is pivotable relative to the main body about an axis in the lateral direction;
    a carrier movably coupled to the main body such that it moves proximally and distally in a longitudinal direction along the main body, the carrier being linked to the trigger such that when the trigger is moved proximally toward the handle, the carrier is pulled proximally along the main body by the trigger, the carrier having a fin that slides in a longitudinal slot at the top side of the main body; and
    a dog pivotably mounted to the carrier, the dog having a toothed engagement surface configured to pinch a band between itself and a vertically extending surface of the carrier, wherein the dog is pivotable about an axis in the vertical direction between an open position and a closed position; and the distal end of the main body includes: a vertically extending slot accessible by the band; chamfered lead in surfaces on either side of the slot; angled faces on either side of the slot; and distal edges having a rounded profile.

* * * * *